(12) United States Patent
Zhang et al.

(10) Patent No.: US 11,615,891 B2
(45) Date of Patent: Mar. 28, 2023

(54) HEART FAILURE EVENT RATE ASSESSMENT

(71) Applicant: Cardiac Pacemakers, Inc., St. Paul, MN (US)

(72) Inventors: Yi Zhang, Plymouth, MN (US); Qi An, Blaine, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 342 days.

(21) Appl. No.: 15/961,209

(22) Filed: Apr. 24, 2018

(65) Prior Publication Data

US 2018/0315509 A1     Nov. 1, 2018

Related U.S. Application Data

(60) Provisional application No. 62/492,172, filed on Apr. 29, 2017.

(51) Int. Cl.
*G16H 50/30* (2018.01)
*A61B 5/02* (2006.01)
*A61B 7/04* (2006.01)
*A61B 5/0245* (2006.01)
*A61B 5/349* (2021.01)
(Continued)

(52) U.S. Cl.
CPC .............. *G16H 50/30* (2018.01); *A61B 5/02* (2013.01); *A61B 5/7264* (2013.01); *A61B 5/7275* (2013.01); *A61B 5/7282* (2013.01); *A61B 5/746* (2013.01); *A61N 1/3627* (2013.01); *A61B 5/0245* (2013.01); *A61B 5/02405* (2013.01);
(Continued)

(58) Field of Classification Search
CPC ........ G16H 50/30; A61B 5/02; A61B 5/7264; A61B 5/7275; A61B 5/7282; A61B 5/746; A61B 5/02405; A61B 5/0245; A61B 5/0452; A61B 5/686; A61B 7/04; A61N 1/3627
USPC .......................................................... 705/2
See application file for complete search history.

(56) References Cited

U.S. PATENT DOCUMENTS

| | | |
|---|---|---|
| 917,078 A | 4/1909 | Kroedel |
| 1,596,120 A | 8/1926 | Poindexter, Jr. |

(Continued)

FOREIGN PATENT DOCUMENTS

| | | |
|---|---|---|
| AU | 2009293198 | 10/2013 |
| CN | 101720244 A | 6/2010 |

(Continued)

OTHER PUBLICATIONS

"U.S. Appl. No. 11/616,430, Examiner Interview Summary dated Apr. 16, 2013", 3 pgs.

(Continued)

*Primary Examiner* — Michael Tomaszewski
*Assistant Examiner* — Rachael Sojin Stone
(74) *Attorney, Agent, or Firm* — Schwegman Lundberg & Woessner, P.A.

(57) ABSTRACT

This document discusses, among other things, systems and methods to determine an alert state for each of a plurality of patients using received physiologic information, determine an event rate for the plurality of patients for a specific alert state, and adjust a composite HF risk determination for the plurality of patients using the determined event rate.

20 Claims, 5 Drawing Sheets

(51) Int. Cl.
    *A61B 5/00*            (2006.01)
    *A61N 1/362*         (2006.01)
    *A61B 5/024*         (2006.01)

(52) U.S. Cl.
    CPC ............... *A61B 5/349* (2021.01); *A61B 5/686* (2013.01); *A61B 7/04* (2013.01)

(56) References Cited

U.S. PATENT DOCUMENTS

| | | |
|---|---|---|
| 2,008,581 A | 7/1935 | Dennison et al. |
| 5,718,235 A * | 2/1998 | Golosarsky .......... A61B 5/0205 600/510 |
| 5,788,643 A | 8/1998 | Feldman |
| 6,039,688 A | 3/2000 | Douglas et al. |
| 6,059,724 A * | 5/2000 | Campell ............ A61B 5/7264 600/300 |
| 6,080,106 A | 6/2000 | Lloyd et al. |
| 6,275,727 B1 | 8/2001 | Hopper et al. |
| 6,334,849 B1 | 1/2002 | Sunagawa |
| 6,336,903 B1 | 1/2002 | Bardy |
| 6,409,675 B1 | 6/2002 | Turcott |
| 6,438,408 B1 | 8/2002 | Mulligan et al. |
| 6,454,705 B1 | 9/2002 | Cosentino et al. |
| 6,459,929 B1 | 10/2002 | Hopper et al. |
| 6,473,646 B2 | 10/2002 | Sun et al. |
| 6,473,647 B1 | 10/2002 | Bradley |
| 6,477,405 B2 | 11/2002 | Kawaguchi |
| 6,527,729 B1 | 3/2003 | Turcott |
| 6,539,249 B1 | 3/2003 | Kadhiresan et al. |
| 6,556,977 B1 | 4/2003 | Lapointe et al. |
| 6,561,984 B1 | 5/2003 | Turcott |
| 6,643,548 B1 | 11/2003 | Mai et al. |
| 6,645,153 B2 | 11/2003 | Kroll et al. |
| 6,678,669 B2 | 1/2004 | Lapointe et al. |
| 6,741,885 B1 | 5/2004 | Park et al. |
| 6,748,261 B1 | 6/2004 | Kroll et al. |
| 6,811,537 B2 | 11/2004 | Bardy |
| 6,821,249 B2 | 11/2004 | Cassceils, III et al. |
| 6,908,437 B2 | 6/2005 | Bardy |
| 6,952,611 B2 | 10/2005 | Sun et al. |
| 6,961,615 B2 | 11/2005 | Kroll et al. |
| 6,980,851 B2 | 12/2005 | Zhu et al. |
| 6,993,377 B2 | 1/2006 | Flick et al. |
| 7,010,347 B2 | 3/2006 | Schecter |
| 7,107,093 B2 | 9/2006 | Burnes |
| 7,115,096 B2 | 10/2006 | Siejko et al. |
| 7,127,290 B2 | 10/2006 | Girouard et al. |
| 7,146,206 B2 | 12/2006 | Glass et al. |
| 7,155,277 B1 * | 12/2006 | Brewer .................. G16H 10/60 607/2 |
| 7,272,443 B2 | 9/2007 | Min et al. |
| 7,308,309 B1 | 12/2007 | Koh |
| 7,313,433 B2 | 12/2007 | Yu et al. |
| 7,431,699 B2 | 10/2008 | Siejko et al. |
| 7,512,439 B1 | 3/2009 | Farazi |
| 7,599,741 B2 | 10/2009 | Hopper et al. |
| 7,629,889 B2 | 12/2009 | Sachanandani et al. |
| 7,761,158 B2 | 7/2010 | Brockway et al. |
| 7,826,899 B1 | 11/2010 | Ryu et al. |
| 7,853,456 B2 | 12/2010 | Soto et al. |
| 8,060,197 B2 | 11/2011 | Ben-David et al. |
| 8,090,562 B2 | 1/2012 | Snider et al. |
| 8,211,033 B2 | 7/2012 | Siejko et al. |
| 8,223,023 B2 | 7/2012 | Sachanandani et al. |
| 8,249,709 B2 | 8/2012 | Davenport et al. |
| 8,257,271 B2 | 9/2012 | Siejko et al. |
| 8,317,717 B2 | 11/2012 | Siejko et al. |
| 8,319,648 B2 | 11/2012 | Siejko et al. |
| 8,346,360 B2 | 1/2013 | Libbus et al. |
| 8,364,263 B2 | 1/2013 | Patangay et al. |
| 8,369,937 B2 | 2/2013 | Bardy |
| 8,469,898 B2 | 6/2013 | Zhang et al. |
| 8,500,650 B2 | 8/2013 | Siejko et al. |
| 8,768,718 B2 | 7/2014 | Cazares et al. |
| 8,798,746 B2 | 8/2014 | Shoreview et al. |
| 9,351,647 B2 | 5/2016 | Zhang et al. |
| 9,622,664 B2 | 4/2017 | An et al. |
| 9,968,266 B2 | 5/2018 | An et al. |
| 10,143,385 B2 | 12/2018 | Sweeney et al. |
| 2001/0001808 A1 | 5/2001 | Chassaing et al. |
| 2002/0016550 A1 | 2/2002 | Sweeney et al. |
| 2002/0029002 A1 | 3/2002 | Bardy |
| 2002/0046002 A1 | 4/2002 | Tang et al. |
| 2002/0099302 A1 * | 7/2002 | Bardy .................. A61B 5/0002 600/510 |
| 2003/0055461 A1 | 3/2003 | Girouard et al. |
| 2003/0083556 A1 | 5/2003 | Cosentino et al. |
| 2003/0092975 A1 | 5/2003 | Casscells, III et al. |
| 2004/0034286 A1 | 2/2004 | Kasper et al. |
| 2004/0039261 A1 * | 2/2004 | Bardy .................. A61B 5/0031 600/300 |
| 2004/0103001 A1 * | 5/2004 | Mazar .................. A61B 5/0002 705/2 |
| 2004/0122297 A1 * | 6/2004 | Stahmann .......... A61B 5/02055 600/300 |
| 2004/0122485 A1 | 6/2004 | Stahmann et al. |
| 2004/0128161 A1 | 7/2004 | Mazar et al. |
| 2004/0133079 A1 * | 7/2004 | Mazar .................. A61B 5/0031 600/300 |
| 2004/0133080 A1 | 7/2004 | Mazar |
| 2004/0147982 A1 | 7/2004 | Bardy |
| 2004/0230127 A1 | 11/2004 | Bardy |
| 2004/0236188 A1 * | 11/2004 | Hutchinson .......... A61B 5/0002 600/300 |
| 2005/0010098 A1 | 1/2005 | Frigstad et al. |
| 2005/0023452 A1 | 2/2005 | Hashimoto et al. |
| 2005/0080348 A1 | 4/2005 | Stahmann et al. |
| 2005/0085734 A1 | 4/2005 | Tehrani |
| 2005/0137481 A1 * | 6/2005 | Sheard ................ A61B 5/0002 600/508 |
| 2005/0142591 A1 | 6/2005 | Ackerman |
| 2005/0143633 A1 | 6/2005 | Jelliffe et al. |
| 2005/0148896 A1 | 7/2005 | Siejko et al. |
| 2005/0149136 A1 | 7/2005 | Siejko et al. |
| 2005/0182657 A1 | 8/2005 | Abraham-Fuchs et al. |
| 2005/0203773 A1 | 9/2005 | Soto et al. |
| 2005/0256550 A1 | 11/2005 | Gilkerson et al. |
| 2006/0010090 A1 | 1/2006 | Brockway et al. |
| 2006/0017575 A1 | 1/2006 | McAdams |
| 2006/0030890 A1 | 2/2006 | Cosentino et al. |
| 2006/0058966 A1 * | 3/2006 | Bruckner ............. G01N 33/574 702/19 |
| 2006/0064030 A1 | 3/2006 | Cosentino et al. |
| 2006/0064136 A1 | 3/2006 | Wang |
| 2006/0074462 A1 | 4/2006 | Verhoef |
| 2006/0089679 A1 | 4/2006 | Zhu et al. |
| 2006/0116557 A1 | 6/2006 | Moore et al. |
| 2006/0142667 A1 | 6/2006 | Munk |
| 2006/0200007 A1 * | 9/2006 | Brockway ................ A61B 5/00 600/300 |
| 2006/0241510 A1 * | 10/2006 | Halperin ................ A61B 5/113 600/534 |
| 2006/0241712 A1 | 10/2006 | Cates et al. |
| 2006/0253006 A1 | 11/2006 | Bardy |
| 2006/0271116 A1 | 11/2006 | Stahmann et al. |
| 2007/0073181 A1 | 3/2007 | Pu et al. |
| 2007/0078491 A1 | 4/2007 | Siejko et al. |
| 2007/0142732 A1 | 6/2007 | Brockway et al. |
| 2007/0213599 A1 | 9/2007 | Siejko et al. |
| 2007/0260285 A1 | 11/2007 | Libbus et al. |
| 2008/0033260 A1 | 2/2008 | Sheppard et al. |
| 2008/0033303 A1 | 2/2008 | Wariar et al. |
| 2008/0103399 A1 | 5/2008 | Patangay et al. |
| 2008/0103406 A1 | 5/2008 | Kameli |
| 2008/0126124 A1 * | 5/2008 | Schechter ............. G06Q 50/22 705/2 |
| 2008/0147140 A1 | 6/2008 | Ternes et al. |
| 2008/0157980 A1 | 7/2008 | Sachanandani et al. |
| 2008/0161700 A1 | 7/2008 | Sachanandani et al. |
| 2008/0162182 A1 | 7/2008 | Cazares et al. |
| 2008/0228090 A1 | 9/2008 | Wariar et al. |
| 2008/0294209 A1 | 11/2008 | Thompson et al. |

(56) References Cited

U.S. PATENT DOCUMENTS

| | | |
|---|---|---|
| 2008/0312541 A1 | 12/2008 | Lewicke et al. |
| 2009/0018461 A1 | 1/2009 | Siejko et al. |
| 2009/0099426 A1 | 4/2009 | Sachanandani et al. |
| 2009/0192561 A1 | 7/2009 | Bauer |
| 2009/0299155 A1 | 12/2009 | Yang et al. |
| 2010/0010522 A1 | 1/2010 | Shturman et al. |
| 2010/0010552 A1 | 1/2010 | Wilson et al. |
| 2010/0030293 A1 | 2/2010 | Sarkar et al. |
| 2010/0045467 A1 | 2/2010 | Jon et al. |
| 2010/0073170 A1 | 3/2010 | Siejko et al. |
| 2010/0076321 A1 | 3/2010 | Zhang et al. |
| 2010/0094102 A1 | 4/2010 | Zhang et al. |
| 2010/0152608 A1 | 6/2010 | Hatlestad |
| 2010/0256463 A1 | 10/2010 | Greenwald et al. |
| 2011/0009753 A1 | 1/2011 | Zhang et al. |
| 2011/0009760 A1 | 1/2011 | Zhang et al. |
| 2011/0082378 A1 | 4/2011 | Messier et al. |
| 2011/0105860 A1 | 5/2011 | Houben et al. |
| 2011/0178565 A1 | 7/2011 | Li et al. |
| 2011/0224565 A1 | 9/2011 | Ong et al. |
| 2011/0275942 A1 | 11/2011 | Stahmann et al. |
| 2011/0295084 A1 | 12/2011 | Thakur et al. |
| 2011/0319726 A1 | 12/2011 | Sachanandani et al. |
| 2012/0011382 A1 | 1/2012 | Volpe et al. |
| 2012/0022387 A1 | 1/2012 | Baida |
| 2012/0109243 A1 | 5/2012 | Hettrick et al. |
| 2012/0157797 A1 | 6/2012 | Zhang et al. |
| 2012/0157799 A1 | 6/2012 | Patangay et al. |
| 2012/0157856 A1 | 6/2012 | An et al. |
| 2012/0157864 A1 | 6/2012 | Thakur et al. |
| 2012/0165890 A1 | 6/2012 | Min |
| 2012/0253207 A1 | 10/2012 | Sarkar et al. |
| 2012/0271183 A1 | 10/2012 | Sachanandani et al. |
| 2012/0271186 A1 | 10/2012 | Siejko et al. |
| 2012/0296228 A1 | 11/2012 | Zhang et al. |
| 2013/0041269 A1 | 2/2013 | Stahmann et al. |
| 2013/0116578 A1* | 5/2013 | An .................. A61B 5/7275 |
| | | 600/484 |
| 2013/0197378 A1 | 8/2013 | Dumont et al. |
| 2013/0204328 A1 | 8/2013 | Stahmann et al. |
| 2013/0226011 A1 | 8/2013 | Zhang et al. |
| 2013/0245466 A1 | 9/2013 | Sachanandani et al. |
| 2013/0339457 A1 | 12/2013 | Freire et al. |
| 2014/0031643 A1 | 1/2014 | An et al. |
| 2014/0343438 A1 | 11/2014 | Sweeney et al. |
| 2014/0343439 A1 | 11/2014 | Sweeney et al. |
| 2015/0126883 A1 | 5/2015 | An et al. |
| 2016/0228072 A1 | 8/2016 | Zhang et al. |
| 2016/0361026 A1 | 12/2016 | Sarkar et al. |
| 2017/0027527 A1 | 2/2017 | Bhat et al. |
| 2017/0235910 A1* | 8/2017 | Cantillon ............... G16H 50/30 |
| | | 705/2 |
| 2017/0357771 A1* | 12/2017 | Connolly ............... G16H 50/30 |
| 2018/0192894 A1 | 7/2018 | An et al. |
| 2020/0187865 A1* | 6/2020 | Sharma ................ A61B 5/7275 |
| 2020/0405244 A1* | 12/2020 | Hettrick ............... A61B 5/7275 |
| 2022/0265219 A1 | 8/2022 | An et al. |

FOREIGN PATENT DOCUMENTS

| | | |
|---|---|---|
| CN | 101765400 A | 6/2010 |
| CN | 102176861 A | 9/2011 |
| CN | 102355852 A | 2/2012 |
| CN | 104661588 A | 5/2015 |
| CN | 105246397 A | 1/2016 |
| CN | 105873499 A | 8/2016 |
| CN | 105873504 A | 8/2016 |
| CN | 106455995 A | 2/2017 |
| CN | 106461636 A | 2/2017 |
| CN | 104661588 B | 3/2017 |
| CN | ZL201380050380.3 | 3/2017 |
| CN | 106725343 A | 5/2017 |
| CN | 105246397 B | 5/2018 |
| CN | 110868911 A | 3/2020 |
| CN | 110868911 B | 10/2022 |
| EP | 0917078 A1 | 5/1999 |
| EP | 1505816 A1 | 2/2005 |
| EP | 2008581 B1 | 8/2011 |
| EP | 2187807 B1 | 6/2012 |
| EP | 2877086 A1 | 6/2015 |
| JP | 2006510447 A | 3/2006 |
| JP | 2006510451 A | 3/2006 |
| JP | 2006292623 A | 10/2006 |
| JP | 2007053436 A | 3/2007 |
| JP | 2007534363 A | 11/2007 |
| JP | 2008053660 A | 3/2008 |
| JP | 2008520340 A | 6/2008 |
| JP | 2008536607 A | 9/2008 |
| JP | 2009518731 A | 5/2009 |
| JP | 2010514497 A | 5/2010 |
| JP | 2010514498 A | 5/2010 |
| JP | 2012502752 | 2/2012 |
| JP | 2015529488 A | 10/2015 |
| JP | 2016523600 A | 8/2016 |
| JP | 6190047 B2 | 8/2017 |
| JP | 6283670 B2 | 2/2018 |
| WO | WO-0197909 A2 | 12/2001 |
| WO | WO-2004056301 A2 | 7/2004 |
| WO | WO-2005110213 A2 | 11/2005 |
| WO | WO-2006026383 A2 | 3/2006 |
| WO | WO-2006084196 A2 | 8/2006 |
| WO | WO-2008085308 A1 | 7/2008 |
| WO | WO-2008121185 A1 | 10/2008 |
| WO | WO-2010033699 A1 | 3/2010 |
| WO | WO-2014018165 A1 | 1/2014 |
| WO | WO-2014189885 A1 | 11/2014 |
| WO | WO-2018200470 A1 | 11/2018 |

OTHER PUBLICATIONS

"U.S. Appl. No. 11/616,430, Examiner Interview Summary dated Dec. 3, 2012", 3 pgs.

"U.S. Appl. No. 11/616,430, Final Office Action dated Mar. 14, 2013", 20 pgs.

"U.S. Appl. No. 11/616,430, Final Office Action dated Dec. 17, 2010", 17 pgs.

"U.S. Appl. No. 11/616,430, Non Final Office Action dated Jul. 18, 2013", 27 pgs.

"U.S. Appl. No. 11/616,430, Non Final Office Action dated Sep. 4, 2012", 19 pgs.

"U.S. Appl. No. 11/616,430, Non-Final Office Action dated Jun. 23, 2010", 22 pgs.

"U.S. Appl. No. 11/616,430, Notice of Allowance dated Feb. 19, 2014", 19 pgs.

"U.S. Appl. No. 11/616,430, Preliminary Amendment filed Jan. 8, 2007", 3 pgs.

"U.S. Appl. No. 11/616,430, Response filed Mar. 16, 2011 to Final Office Action dated Dec. 17, 2010", 16 pgs.

"U.S. Appl. No. 11/616,430, Response filed May 23, 2013 to Final Office Action dated Mar. 14, 2013", 13 pgs.

"U.S. Appl. No. 11/616,430, Response filed Sep. 23, 2010 to Non-Final Office Action dated Jun. 23, 2010", 18 pgs.

"U.S. Appl. No. 11/616,430, Response filed Oct. 18, 2013 to Non Final Office Action dated Jul. 18, 2013", 14 pgs.

"U.S. Appl. No. 11/616,430, Response filed Nov. 28, 2012 to Non Final Office Action dated Sep. 4, 2012", 14 pgs.

"U.S. Appl. No. 11/616,441, Final Office Action dated Aug. 3, 2010", 8 pgs.

"U.S. Appl. No. 11/616,441, Non-Final Office Action dated Feb. 24, 2010", 11 pgs.

"U.S. Appl. No. 11/616,441, Response filed Jan. 15, 2010 to Restriction Requirement dated Dec. 16, 2009", 8 pgs.

"U.S. Appl. No. 11/616,441, Response filed May 24, 2010 to Non Final Office Action dated Feb. 24, 2010", 14 pgs.

"U.S. Appl. No. 11/616,441, Response filed Dec. 14, 2010 to Final Office Action dated Aug. 3, 2010", 11 pgs.

"U.S. Appl. No. 11/616,441, Restriction Requirement dated Dec. 16, 2009", 5 pgs.

(56) References Cited

OTHER PUBLICATIONS

"U.S. Appl. No. 11/616,450, Non Final Office Action dated Mar. 4, 2009", 8 pgs.
"U.S. Appl. No. 11/616,450, Notice of Allowance dated Jul. 27, 2009.", 4 pgs.
"U.S. Appl. No. 11/616,450, Response filed Jun. 4, 2009 to Non Final Office Action dated Mar. 4, 2009", 13 pgs.
"U.S. Appl. No. 12/561,721, Non Final Office Action dated Feb. 29, 2012", 8 pgs.
"U.S. Appl. No. 12/561,721, Non Final Office Action dated Oct. 16, 2012", 7 pgs.
"U.S. Appl. No. 12/561,721, Non-Final Office Actions dated Apr. 29, 2011", 6 pgs.
"U.S. Appl. No. 12/561,721, Notice of Allowance dated Feb. 22, 2013", 5 pgs.
"U.S. Appl. No. 12/561,721, Response filed Jan. 16, 2013 to Non Final Office Action dated Oct. 16, 2012", 9 pgs.
"U.S. Appl. No. 12/561,721, Response filed May 22, 2012 to Non Final Office Action dated Feb. 29, 2012", 9 pgs.
"U.S. Appl. No. 12/561,721, Response filed Aug. 29, 2011 to Non-Final Office Action dated Apr. 29, 2011", 13 pgs.
"U.S. Appl. No. 12/613,007, Final Office Action dated May 5, 2011", 6 pgs.
"U.S. Appl. No. 12/613,007, Non-Final Office Action dated Jan. 21, 2011", 7 pgs.
"U.S. Appl. No. 12/613,007, Notice of Allowance dated Jun. 3, 2011", 5 pgs.
"U.S. Appl. No. 12/613,007, Response filed Apr. 21, 2011 to Non-Final Office Action dated Jan. 21, 2011", 11 pgs.
"U.S. Appl. No. 12/613,007, Response filed May 24, 2011 to Final Office Action dated May 5, 2011", 7 pgs.
"U.S. Appl. No. 12/776,557, Corrected Notice of Allowability dated Jul. 12, 2012", 4 pgs.
"U.S. Appl. No. 12/776,557, Notice of Allowance dated May 11, 2012", 7 pgs.
"U.S. Appl. No. 12/776,557, Response filed Apr. 9, 2012 to Non Final Office Action dated Jan. 19, 2012", 9 pgs.
"U.S. Appl. No. 13/229,110, Non Final Office Action dated Dec. 5, 2011", 7 pgs.
"U.S. Appl. No. 13/229,110, Notice of Allowance dated Mar. 20, 2012", 5 pgs.
"U.S. Appl. No. 13/229,110, Response filed Mar. 2, 2012 to Non Final Office Action dated Dec. 5, 2011", 9 pgs.
"U.S. Appl. No. 13/726,786, Advisory Action dated Jan. 26, 2017", 3 pgs.
"U.S. Appl. No. 13/726,786, Corrected Notice of Allowance dated Jan. 4, 2018", 3 pgs.
"U.S. Appl. No. 13/726,786, Examiner Interview Summary dated Oct. 13, 2017", 3 pgs.
"U.S. Appl. No. 13/726,786, Final Office Action dated Jul. 16, 2015", 25 pgs.
"U.S. Appl. No. 13/726,786, Final Office Action dated Sep. 14, 2017", 28 pgs.
"U.S. Appl. No. 13/726,786, Final Office Action dated Oct. 13, 2016", 24 pgs.
"U.S. Appl. No. 13/726,786, Non Final Office Action dated Jan. 2, 2015", 19 pgs.
"U.S. Appl. No. 13/726,786, Non Final Office Action dated May 19, 2016", 24 pgs.
"U.S. Appl. No. 13/726,786, Non Final Office Action dated Jun. 12, 2017", 24 pgs.
"U.S. Appl. No. 13/726,786, Notice of Allowance dated Dec. 28, 2017", 13 pgs.
"U.S. Appl. No. 13/726,786, Response filed Mar. 23, 2015 to Non Final Office Action dated Jan. 2, 2015", 13 pgs.
"U.S. Appl. No. 13/726,786, Response filed Jul. 21, 2016 to Non Final Office Action dated May 19, 2016", 11 pgs.
"U.S. Appl. No. 13/726,786, Response filed Sep. 5, 2017 to Non Final Office Action dated Jun. 12, 2017", 16 pgs.
"U.S. Appl. No. 13/726,786, Response filed Oct. 20, 2015 to Final Office Action dated Jul. 16, 2015", 17 pgs.
"U.S. Appl. No. 13/726,786, Response filed Dec. 7, 2017 to Final Office Action dated Sep. 14, 2017", 19 pgs.
"U.S. Appl. No. 13/726,786, Response filed Dec. 13, 2016 to Final Office Action dated Oct. 13, 2016", 13 pgs.
"U.S. Appl. No. 13/858,631, Final Office Action dated Oct. 22, 2015", 6 pgs.
"U.S. Appl. No. 13/858,631, Non Final Office Action dated May 29, 2015", 10 pgs.
"U.S. Appl. No. 13/858,631, Notice of Allowance dated Feb. 4, 2016", 5 pgs.
"U.S. Appl. No. 13/858,631, Preliminary Amendment filed Apr. 9, 2013", 8 pgs.
"U.S. Appl. No. 13/858,631, Response filed Aug. 31, 2015 to Non Final Office Action dated May 29, 2015", 14 pgs.
"U.S. Appl. No. 13/858,631, Response filed Dec. 14, 2015 to Final Office Action dated Oct. 22, 2015", 8 pgs.
"U.S. Appl. No. 13/912,541, Advisory Action dated Oct. 25, 2016", 3 pgs.
"U.S. Appl. No. 13/912,541, Advisory Action dated Dec. 22, 2017", 5 pgs.
"U.S. Appl. No. 13/912,541, Examiner Interview Summary dated Sep. 28, 2016", 3 pgs.
"U.S. Appl. No. 13/912,541, Final Office Action dated Aug. 5, 2016", 25 pgs.
"U.S. Appl. No. 13/912,541, Final Office Action dated Aug. 24, 2017", 29 pgs.
"U.S. Appl. No. 13/912,541, Non Final Office Action dated Feb. 8, 2018", 27 pgs.
"U.S. Appl. No. 13/912,541, Non Final Office Action dated Feb. 9, 2017", 29 pgs.
"U.S. Appl. No. 13/912,541, Non Final Office Action dated Feb. 11, 2016", 24 pgs.
"U.S. Appl. No. 13/912,541, Response filed Jan. 24, 2018 to Final Office Action dated Aug. 24, 2017", 17 pgs.
"U.S. Appl. No. 13/912,541, Response filed May 2, 2016 to Non Final Office Action dated Feb. 11, 2016", 15 pgs.
"U.S. Appl. No. 13/912,541, Response filed May 9, 2017 to Non Final Office Action dated Feb. 9, 2017", 18 pgs.
"U.S. Appl. No. 13/912,541, Response filed Oct. 3, 2016 to Final Office Action dated Aug. 5, 2016", 14 pgs.
"U.S. Appl. No. 13/912,541, Response filed Nov. 21, 2017 to Final Office Action dated Aug. 24, 2017", 16 pgs.
"U.S. Appl. No. 13/912,541, Response filed Dec. 5, 2016 to Advisory Action dated Oct. 25, 2016", 8 pgs.
"U.S. Appl. No. 14/282,283, Advisory Action dated Oct. 20, 2017", 3 pgs.
"U.S. Appl. No. 14/282,283, Final Office Action dated Aug. 1, 2017", 12 pgs.
"U.S. Appl. No. 14/282,283, Non Final Office Action dated Jan. 30, 2017", 13 pgs.
"U.S. Appl. No. 14/282,283, Reponse filed Oct. 2, 2017 to Final Office Action dated Aug. 1, 2017", 11 pgs.
"U.S. Appl. No. 14/282,283, Response filed Apr. 13, 2017 to Non Final Office Action dated Jan. 30, 2017", 12 pgs.
"U.S. Appl. No. 14/282,353, Examiner Interview Summary dated Sep. 28, 2017", 2 pgs.
"U.S. Appl. No. 14/282,353, Non Final Office Action dated Feb. 8, 2018", 8 pgs.
"U.S. Appl. No. 14/282,353, Non Final Office Action dated Jul. 6, 2017", 19 pgs.
"U.S. Appl. No. 14/282,353, Response filed Jun. 19, 2017 to Restriction Requirement dated Apr. 21, 2017", 3 pgs.
"U.S. Appl. No. 14/282,353, Response filed Oct. 3, 2017 to Non Final Office Action dated Jul. 6, 2017", 13 pgs.
"U.S. Appl. No. 14/282,353, Restriction Requirement dated Apr. 21, 2017", 6 pgs.
"U.S. Appl. No. 14/510,392, Advisory Action dated Jul. 8, 2016", 3 pgs.
"U.S. Appl. No. 14/510,392, Final Office Action dated May 2, 2016", 13 pgs.

(56) References Cited

OTHER PUBLICATIONS

"U.S. Appl. No. 14/510,392, Non Final Office Action dated Oct. 5, 2015", 12 pgs.
"U.S. Appl. No. 14/510,392, Notice of Allowance dated Dec. 16, 2016", 5 pgs.
"U.S. Appl. No. 14/510,392, Response filed Jan. 5, 2016 to Non Final Office Action dated Oct. 5, 2015", 13 pgs.
"U.S. Appl. No. 14/510,392, Response filed Jun. 30, 2016 to Final Office Action dated May 2, 2016", 13 pgs.
"U.S. Appl. No. 15/132,738, Preliminary Amendment filed Apr. 26, 2016", 6 pgs.
"U.S. Appl. No. 15/911,856, Preliminary Amendment filed Mar. 12, 2018", 6 pgs.
"Application Serial No. PCT/US2014/038720, International Preliminary Report on Patentability dated Dec. 3, 2015", 6 pgs.
"Australian Application Serial No. 2007342523, Examiner Report dated Jan. 20, 2011", 2 pgs.
"Australian Application Serial No. 2007342523, First Examiner Report dated May 21, 2010", 3 pgs.
"Australian Application Serial No. 2007342523, Request to Amend a Complete Specification filed May 20, 2011", 17 pgs.
"Australian Application Serial No. 2007342523, Response filed Dec. 23, 2010 to First Examiner Report dated May 21, 2010", 21 pgs.
"Australian Application Serial No. 2007342524, First Examiner Report dated Apr. 21, 2010", 1 pg.
"Australian Application Serial No. 2007342524, Notice of Acceptance dated Jul. 8, 2010", 8 pgs.
"Australian Application Serial No. 2007342524, Request to Amend and Second Statement of Proposed Amendments filed Jun. 17, 2010", 17 pgs.
"Australian Application Serial No. 2009293198, Office Action dated May 7, 2012", 3 pgs.
"Australian Application Serial No. 2009293198, Response filed Apr. 2, 2013 to Non Final Office Action dated Nov. 22, 2012", 16.
"Australian Application Serial No. 2009293198, Response filed Oct. 8, 2012 to Non Final Office Action dated May 7, 2012", 18.
"Australian Application Serial No. 2009293198, Subsequent Examiners Report dated Dec. 7, 2012", 8 pgs.
"Chinese Application Serial No. 200780048870.4, Office action dated Jun. 12, 2010", (w/ English Translation), 8 pgs.
"Chinese Application Serial No. 200780048870.4, Response filed Oct. 21, 2010 to Office Action dated Jun. 12, 2010", 16 pgs.
"Chinese Application Serial No. 201380050380.3, Office Action dated May 4, 2016", With English Translation, 12 pgs.
"Chinese Application Serial No. 201380050380.3, Response filed Sep. 13, 2016 to Office Action dated May 4, 2016", with amended English claims, 17 pgs.
"Chinese Application Serial No. 201480029099.6, Office Action dated Mar. 14, 2017", w/ English translation, 18 pgs.
"Chinese Application Serial No. 201480029099.6, Office Action dated Dec. 5, 2017", W/ English Translation, 15 pgs.
"Chinese Application Serial No. 201480029099.6, Response filed Feb. 13, 2018 to Office Action dated Dec. 5, 2017", w/ claims in English, 14 pgs.
"Chinese Application Serial No. 201480029099.6, Response filed Jul. 28, 2017 to Office Action dated Mar. 14, 2017", w/ claims in English, 15 pgs.
"European Application Serial No. 07862948.2, Office Action dated Dec. 19, 2011", 5 pgs.
"European Application Serial No. 07862948.2, Response filed Apr. 30, 2012 to Office Action dated Dec. 19, 2011", 19 pgs.
"European Application Serial No. 07862949.0, Office Action dated Jun. 30, 2010", 5 pgs.
"European Application Serial No. 07862949.0, Response filed Dec. 21, 2010 to Office Action dated Jun. 30, 2010", 16 pgs.
"European Application Serial No. 09792660.4, Office Action Response filed Dec. 22, 2011", 14 pgs.
"International Application No. PCT/US2007/025666, International Preliminary Report dated Jul. 9, 2009", 7 pgs.
"International Application No. PCT/US2007/025666, International Search Report dated Jun. 16, 2008", 4 pgs.
"International Application No. PCT/US2007/025666, Written Opinion dated Jun. 16, 2008", 6 pgs.
"International Application No. PCT/US2007/025667, International Search Report dated Jun. 11, 2008", 4 pgs.
"International Application No. PCT/US2007/025667, Written Opinion dated Jun. 11, 2008", 5 pgs.
"International Application No. PCT/US2007/025668, International Search Report dated Apr. 18, 2008", 5 pgs.
"International Application No. PCT/US2007/025668, Written Opinion dated Apr. 18, 2008", 7 pgs.
"International Application Serial No. PCT/US2009/057316 International Preliminary Report on Patentability dated Mar. 31, 2011", 7 pgs.
"International Application Serial No. PCT/US2009/057316, International Search Report dated Dec. 23, 2009", 5 pgs.
"International Application Serial No. PCT/US2009/057316, Written Opinion dated Dec. 23, 2009", 8 pgs.
"International Application Serial No. PCT/US2013/044680, International Preliminary Report on Patentability dated Feb. 5, 2015", 9 pgs.
"International Application Serial No. PCT/US2013/044680, International Search Report dated Oct. 10, 2013", 4 pgs.
"International Application Serial No. PCT/US2013/044680, Written Opinion dated Oct. 10, 2013", 7 pgs.
"International Application Serial No. PCT/US2014/038720, International Search Report dated Jul. 21, 2014".
"International Application Serial No. PCT/US2014/038720, Written Opinion dated Jul. 21, 2014".
"Japanese Application Serial No. 2009-544022, Office Action dated Oct. 11, 2011", (W/ English Translation), 4 pgs.
"Japanese Application Serial No. 2009-544022, Response filed Jan. 11, 2012 to Office Action dated Oct. 11, 2011", (W/ English Translation of Amended Claims), 9 pgs.
"Japanese Application Serial No. 2009-544022, Voluntary Amendment filed Jun. 29, 2009", (W/ English Translation), 71 pgs.
"Japanese Application Serial No. 2011-527959, Office Action dated Feb. 19, 2013", (w/ English Translation), 6 pgs.
"Japanese Application Serial No. 2015-524260, Office Action dated May 9, 2017", w/ English translation, 8 pgs.
"Japanese Application Serial No. 2015-524260, Response filed Jul. 31, 2017 to Office Action dated May 9, 2017", w/ claims in English, 14 pgs.
"Japanese Application Serial No. 2016-514999, Office Action dated Nov. 1, 2016", Without English Translation, 3 pgs.
"Japanese Application Serial No. 2016-514999, Response filed Feb. 1, 2017 to Office Action dated Nov. 1, 2016", w/ Claims in English, 12 pgs.
Ahmed, S. Sultan, et al., "Systolic Time Intervals as Measures of the Contractile State of the Left Ventricular Myocardium in Man", Circulation, vol. XLVI, Sep. 1972, 559-571.
Anand, I. S, et al., "Design and Performance of a Multisensor Heart Failure Monitoring Algorithm: Results From the Multisensor Monitoring in Congestive Heart Failure (MUSIC) Study", Journal of Cardiac Failure, 18(4), (Apr. 2012), 289-295.
Boehmer, John P., et al., "A Multisensor Algorithm Predicts Heart Failure Events in Patients With Implanted Devices", JACC: Heart Failure, vol. 5, No. 3, 2017, pp. 216-225.
Cazares, S., et al., "Between-Patient Comparisons for Risk Stratification of Future Heart Failure Decompensation", U.S. Appl. No. 11/616,430, filed Dec. 27, 2006, 87 pgs.
Ekman, I., et al., "Exploring Symptoms in Chronic Heart Failure", The European Journal of Heart Failure, 7, (2005), 699-703.
Garrard, et al., "The Relationship of Alterations in Systolic Time Intervals to Ejection Fraction in Patients with Cardiac Disease", Circulation, (1970), 455-462.
Ingle, L., et al., "Perception of Symptoms is Out of Proportion to Cardiac Pathology in Patients With "Diastolic Heart Failure"", Heart, 94, (2008), 748-753.
Lavietes, M., et al., "Dyspnea and Symptom Amplification in Asthma", Respiration, 75(2), (2008), 158-162.

(56) References Cited

OTHER PUBLICATIONS

Sachanandani, H. G., et al., "Inter-Relation Between Within-Patient Decompensation Detection Algorithm and Between-Patient Stratifier to Manage HF Patients in a More Efficient Manner", U.S. Appl. No. 11/616,441, filed Dec. 27, 2006, 87 pgs.
Sachanandani, H. G., et al.. "Within-Patient Algorithm to Predict Heart Failure Decompensation", U.S. Appl. No. 11/616,450, filed Dec. 27, 2006, 86 pgs.
Skotzko, C. E., "Symptom Perception in CHF: (why mind matters)", Heart Failure Reviews, [Epub Dec. 11, 2007], (prior to Jun. 13, 2008), 6 pages.
Waggoner, Alan D., et al., "Improvements in Left Ventricular Diastolic Function After Cardiac Resynchronization Therapy Are Coupled to Response in Systolic Performance", JAAC; vol. 46, No. 12, (Dec. 20, 2005), 2244-2249.
Weissler, Arnold M, et al., "Systolic Time Intervals in Heart Failure in Man", Circulation, vol. XXXVII, No. 2, (Feb. 1968), 149-159.
U.S. Appl. No. 13/726,786, filed Dec. 26, 2012, A Risk Stratification Based Heart Failure Detection Algorithm.
U.S. Appl. No. 15/911,856, filed Mar. 5, 2018, A Risk Stratification Based Heart Failure Detection Algorithm.
U.S. Appl. No. 13/912,541, filed Jun. 7, 2013, Heart Failure Patients Stratification.
U.S. Appl. No. 14/282,353, filed May 20, 2014, Methods and Apparatus for Stratifying Risk of Heart Failure Decompensation.
U.S. Appl. No. 14/510,392 U.S. Pat. No. 9,622,664, filed Oct. 9, 2014, Methods and Apparatus for Detecting Heart Failure Decompensation Event and Stratifying the Risk of the Same.
"U.S. Appl. No. 13/726,786, Examiner Interview Summary dated Apr. 17, 2018", 2 pgs.
"U.S. Appl. No. 13/912,541, Advisory Action dated Dec. 21, 2018", 5 pgs.
"U.S. Appl. No. 13/912,541, Final Office Action dated Sep. 18, 2018", 26 pgs.
"U.S. Appl. No. 13/912,541, Final Office Action dated Nov. 15, 2019", 22 pgs.
"U.S. Appl. No. 13/912,541, Non Final Office Action dated Feb. 4, 2020", 25 pgs.
"U.S. Appl. No. 13/912,541, Non Final Office Action dated Mar. 21, 2019", 20 pgs.
"U.S. Appl. No. 13/912,541, Response filed Jan. 17, 2019 to Final Office Acton dated Sep. 18, 2018", 12 pgs.
"U.S. Appl. No. 13/912,541, Response filed Jan. 21, 2020 to Final Office Action dated Nov. 15, 2019", 14 pgs.
"U.S. Appl. No. 13/912,541, Response filed May 4, 2020 to Non Final Office Action dated Feb. 4, 2020", 14 pgs.
"U.S. Appl. No. 13/912,541, Response filed May 8, 2018 to Non Final Office Action dated Feb. 8, 2018", 15 pgs.
"U.S. Appl. No. 13/912,541, Response filed Jul. 18, 2019 to Non Final Office Action dated Mar. 21, 2019", 12 pgs.
"U.S. Appl. No. 13/912,541, Response filed Nov. 19, 2018 to Final Office Action dated Sep. 18, 2018", 13 pgs.
"U.S. Appl. No. 14/282,353, Notice of Allowance dated Aug. 1, 2018", 13 pgs.
"U.S. Appl. No. 15/911,856, Examiner Interview Summary dated Feb. 26, 2020", 2 pgs.
"U.S. Appl. No. 15/911,856, Non Final Office Action dated Apr. 8, 2020", 9 pgs.
"U.S. Appl. No. 15/911,856, Supplemental Amendment filed Oct. 17, 2019", 11 pgs.
"International Application Serial No. PCT/US2018/029065, International Preliminary Report on Patentability dated Nov. 7, 2019", 8 pgs.
"International Application Serial No. PCT/US2018/029065, International Search Report dated Jul. 2, 2018", 5 pgs.
"International Application Serial No. PCT/US2018/029065, Written Opinion dated Jul. 2, 2018", 6 pgs.
"Physician's technical guide heartlogic TM heart failure diagnostic service", Boston Scientific:, (Sep. 1, 2016).

Samuel, Branders, et al., "A balanced hazard ratio for risk group evaluation from survival data", Statistics in Medicine, (Jul. 30, 2015), 2528-2543.
"U.S. Appl. No. 13/912,541, Examiner Interview Summary dated Sep. 22, 2020", 3 pgs.
"U.S. Appl. No. 13/912,541, Final Office Action dated Aug. 6, 2020", 27 pgs.
"U.S. Appl. No. 13/912,541, Non Final Office Action dated Oct. 28, 2020", 26 pgs.
"U.S. Appl. No. 13/912,541, Response filed Jan. 28, 2021 to Non Final Office Action dated Oct. 28, 2020", 16 pgs.
"U.S. Appl. No. 13/912,541, Response filed Oct. 6, 2020 to Final Office Action dated Aug. 6, 2020", 16 pgs.
"U.S. Appl. No. 15/911,856, Advisory Action dated Sep. 28, 2020", 5 pgs.
"U.S. Appl. No. 15/911,856, Examiner Interview Summary dated Jul. 14, 2020", 4 pgs.
"U.S. Appl. No. 15/911,856, Examiner Interview Summary dated Nov. 30, 2020", 4 pgs.
"U.S. Appl. No. 15/911,856, Final Office Action dated Jul. 20, 2020", 14 pgs.
"U.S. Appl. No. 15/911,856, Response filed Jul. 8, 2020 to Non Final Office Action dated Apr. 8, 2020", 16 pgs.
"U.S. Appl. No. 15/911,856, Response filed Sep. 21, 2020 to Final Office Action dated Jul. 20, 2020", 15 pgs.
"U.S. Appl. No. 15/911,856, Response filed Oct. 15, 2020 to Advisory Action dated Sep. 28, 2020", 16 pgs.
"European Application Serial No. 18726586.3, Response Filed Jun. 10, 2020 to Communication pursuant to Rules 161(1) and 162 EPC dated Dec. 6, 2019", 17 pgs.
Dolan, Brian, "Timeline: The iPhone as a medical tool", [Online], Retrieved from the Internet: <https://www.mobihealthnews.com/2580/timeline-the-iphone-as-medical-tool>, (2010).
Hsia, et al., "Debate: Do all patients with heart failure require implantable defibrillators to prevent sudden death", [Online], Retrieved from the Internet: http://cvm.controlled-trials.com/content/1/2/098>, (2011).
Nagele, et al., "Rate-responsive pacing in patients with heart failure: long-term results of a randomized study", European Society of Cardiology, (2008).
Patel, Shyamal, et al., "A review of wearable sensors and systems with application in rehabilitation", Journal of NeuroEngineering and Rehabilitation 9(21), (2012), 17 pgs.
Sarasohon-Kahn, Jane, "The Connected Patient Charting the Vital Signs of Remote Health Monitoring", California Healthcare Foundation, (2011).
"U.S. Appl. No. 13/912,541, Advisory Action dated Jul. 12, 2021", 3 pgs.
"U.S. Appl. No. 13/912,541, Appeal Brief filed Nov. 16, 2021", 22 pgs.
"U.S. Appl. No. 13/912,541, Decision on Pre-Appeal Brief Request for Review dated Oct. 1, 2021", 2 pgs.
"U.S. Appl. No. 13/912,541, Examiner Interview Summary dated Jul. 1, 2021", 3 pgs.
"U.S. Appl. No. 13/912,541, Final Office Action dated Apr. 26, 2021", 28 pgs.
"U.S. Appl. No. 13/912,541, Pre-Appeal Brief Request filed Aug. 17, 2021", 5 pgs.
"U.S. Appl. No. 13/912,541, Response filed Jun. 28, 2021 to Final Office Action dated Apr. 26, 2021", 14 pgs.
"U.S. Appl. No. 15/911,856, Applicant Interview Summary filed Sep. 27, 2021", 2 pgs.
"U.S. Appl. No. 15/911,856, Examiner Interview Summary dated Jan. 7, 2022", 3 pgs.
"U.S. Appl. No. 15/911,856, Examiner Interview Summary dated Jul. 6, 2021", 3 pgs.
"U.S. Appl. No. 15/911,856, Examiner Interview Summary dated Sep. 27, 2021", 2 pgs.
"U.S. Appl. No. 15/911,856, Final Office Action dated Aug. 31, 2021", 34 pgs.
"U.S. Appl. No. 15/911,856, Final Office Action dated Oct. 18, 2021", 12 pgs.

(56) References Cited

OTHER PUBLICATIONS

"U.S. Appl. No. 15/911,856, Non Final Office Action dated Mar. 25, 2021", 32 pgs.
"U.S. Appl. No. 15/911,856, Response filed Aug. 25, 2021 to Non Final Office Action dated Mar. 25, 2021", 19 pgs.
"Chinese Application Serial No. 201880040684.4, Office Action dated Nov. 30, 2021", with English translation, 30 pgs.
"U.S. Appl. No. 13/912,541, Examiner's Answer dated May 19, 2022", 9 pgs.
"Chinese Application Serial No. 201880040684.4, Response filed Apr. 12, 2022 to Office Action dated Nov. 30, 2021", w/ English Claims, 14 pgs.
"European Application Serial No. 18726586.3, Communication Pursuant to Article 94(3) EPC dated Apr. 6, 2022", 5 pgs.
"U.S. Appl. No. 13/912,541, Reply Brief filed Jul. 19, 2022", 5 pgs.
"U.S. Appl. No. 17/578,097 Preliminary Amendment filed Feb. 1, 2022", 7 pgs.
"Chinese Application Serial No. 201880040684.4, Voluntary Amendment filed Jun. 27, 2022", w/ English Claims, 10 pgs.
"European Application Serial No. 18726586.3, Response filed Aug. 12, 2022 to Communication Pursuant to Article 94(3) EPC dated Apr. 6, 2022", 25 pgs.

* cited by examiner

HEART FAILURE EVENT RATE ASSESSMENT

CLAIM OF PRIORITY

This application claims the benefit of priority under 35 U.S.C. § 119(e) of U.S. Provisional Patent Application Ser. No. 62/492,172, filed on Apr. 29, 2017, which is herein incorporated by reference in its entirety.

TECHNICAL FIELD

This document relates generally to medical devices, and more particularly, but not by way of limitation, to systems, devices, and methods for event rate assessment of congestive heart failure.

BACKGROUND

Congestive heart failure (CHF) can be described as a reduction in ability of the heart to deliver enough blood to meet bodily needs, affecting over five million people in the United States alone. CHF patients commonly have enlarged heart with weakened cardiac muscles, resulting in reduced contractility and poor cardiac output of blood.

CHF is typically a chronic condition, but can also occur suddenly, affecting the left, right, or both sides of a heart. If CHF affects the left ventricle, signals that control the left ventricular contraction can be delayed, causing left ventricular dysfunction, further decreasing the pumping efficiency of the heart.

SUMMARY

This document discusses, among other things, systems and methods to determine an alert state for each of a plurality of patients using received physiologic information, determine an event rate for the plurality of patients for a specific alert state, and adjust a composite HF risk determination for the plurality of patients using the determined event rate An example (e.g., "Example 1") of subject matter (e.g., a medical device) may include a signal receiver circuit configured to receive physiologic information for a plurality of patients; a risk assessment circuit configured to: determine an alert state for each patient using the received physiologic information and a threshold; determine an event rate for the plurality of patients for a specific alert state; and adjust a composite HF risk determination for the plurality of patients using the determined event rate.

In Example 2, the subject matter of Example 1 may optionally be configured such that, to adjust the composite HF risk determination for the plurality of patients, the risk assessment circuit is configured to adjust the threshold using the determined event rate for the specific alert state.

In Example 3, the subject matter any one or more of Examples 1-2 may optionally be configured such that, to adjust the composite HF risk determination for the plurality of patients, the risk assessment circuit is configured to adjust a weighting of a signal metric used to determine the composite HF risk.

In Example 4, the subject matter any one or more of Examples 1-3 may optionally be configured such that the risk assessment circuit is configured to adjust the composite HF risk determination to optimize the determined event rate for the specific alert state.

In Example 5, the subject matter any one or more of Examples 1-4 may optionally be configured such that the alert state includes an IN alert state and an OUT alert state, and the risk assessment circuit may optionally be configured to determine event rates for the plurality of patients for each alert state, and to adjust the composite HF risk determination using the determined event rates.

In Example 6, the subject matter any one or more of Examples 1-5 may optionally be configured such that the risk assessment circuit is configured to determine an event rate ratio using the determined event rates for the IN alert state and OUT alert state, and, to adjust the composite HF risk determination using the determined event rates, the risk assessment circuit may optionally be configured to adjust the composite HF risk determination using the determined event rate ratio.

In Example 7, the subject matter any one or more of Examples 1-6 may optionally be configured such that, to adjust the composite HF risk determination, the risk assessment circuit is configured to adjust the threshold to maximize the event rate ratio, where the event rate ratio is the event rate for the IN alert state divided by the event rate for the OUT alert state.

In Example 8, the subject matter any one or more of Examples 1-7 may optionally be configured such that the risk assessment circuit is configured to determine the event rate using a number of heart failure events in each alert state, wherein the heart failure events include an intervention associated with a congestive heart failure (CHF) condition.

In Example 9, the subject matter any one or more of Examples 1-8 may optionally be configured such that the risk assessment circuit is configured to determine the alert state for each patient using a comparison of the determined composite HF risk to the threshold.

An example (e.g., "Example 10") of subject matter (e.g., a machine-readable medium) may include instructions that, when performed by a medical device, cause the medical device to: receive physiologic information for a plurality of patients; determine an alert state for each patient using the received physiologic information and a threshold; determine an event rate for the plurality of patients for a specific alert state; and adjust a composite HF risk determination for the plurality of patients using the determined event rate.

In Example 11, the subject matter of Example 10 may optionally be configured such that the instructions that, when performed by the medical device, cause the medical device to adjust the composite HF risk determination include instructions to adjust the threshold using the determined event rate for the specific alert state.

In Example 12, the subject matter of any one or more of Examples 10-11 may optionally be configured such that the instructions that, when performed by the medical device, cause the medical device to adjust the composite HF risk determination include instructions to adjust a weighting of a signal metric used to determine the composite HF risk.

In Example 13, the subject matter of any one or more of Examples 10-12 may optionally be configured to include instructions that, when performed by the medical device, cause the medical device to adjust the composite HF risk determination to optimize the determined event rate for the specific alert state.

In Example 14, the subject matter of any one or more of Examples 10-13 may optionally be configured such that the alert state includes an IN alert state and an OUT alert state, and optionally be configured to include instructions that, when performed by the medical device, cause the medical device to: determine event rates for the plurality of patients for each of the IN and OUT alert states; and adjust the composite HF risk determination using the determined event rates.

In Example 15, the subject matter of any one or more of Examples 10-14 may optionally be configured to include instructions that, when performed by the medical device, cause the medical device to: determine an event rate ratio using the determined event rates for the IN alert state and OUT alert state, and adjust the composite HF risk determination using the determined event rate ratio.

An example (e.g., "Example 16") of subject matter (e.g., a method) may include receiving physiologic information for a plurality of patients using a signal receiver circuit, determining, using a risk assessment circuit, an alert state for each patient using the received physiologic information and a threshold; determining, using the risk assessment circuit, an event rate for the plurality of patients for a specific alert state; and adjusting, using the risk assessment circuit, a composite HF risk determination for the plurality of patients using the determined event rate.

In Example 17, the subject matter of Example 16 may optionally be configured such that the adjusting the composite HF risk determination includes adjusting the threshold using the determined event rate for the specific alert state.

In Example 18, the subject matter of any one or more of Examples 16-17 may optionally be configured such that the adjusting the composite HF risk determination includes adjusting a weighting of a signal metric used to determine the composite HF risk.

In Example 19, the subject matter of any one or more of Examples 16-18 may optionally be configured such that the alert state includes an IN alert state and an OUT alert state, wherein the determining the event rate includes determine event rates for the plurality of patients for each alert state, and wherein the adjusting the composite HF risk determination includes using the determined event rates.

In Example 20, the subject matter of any one or more of Examples 16-19 may optionally be configured to include: determining an event rate ratio using the determined event rates for the IN alert state and OUT alert state, wherein the adjusting the composite HF risk determination using the determined event rates includes adjusting the composite HF risk determination using the determined event rate ratio.

An example (e.g., "Example 21") of subject matter (e.g., a system or apparatus) may optionally combine any portion or combination of any portion of any one or more of Examples 1-20 to include "means for" performing any portion of any one or more of the functions or methods of Examples 1-20, or a "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
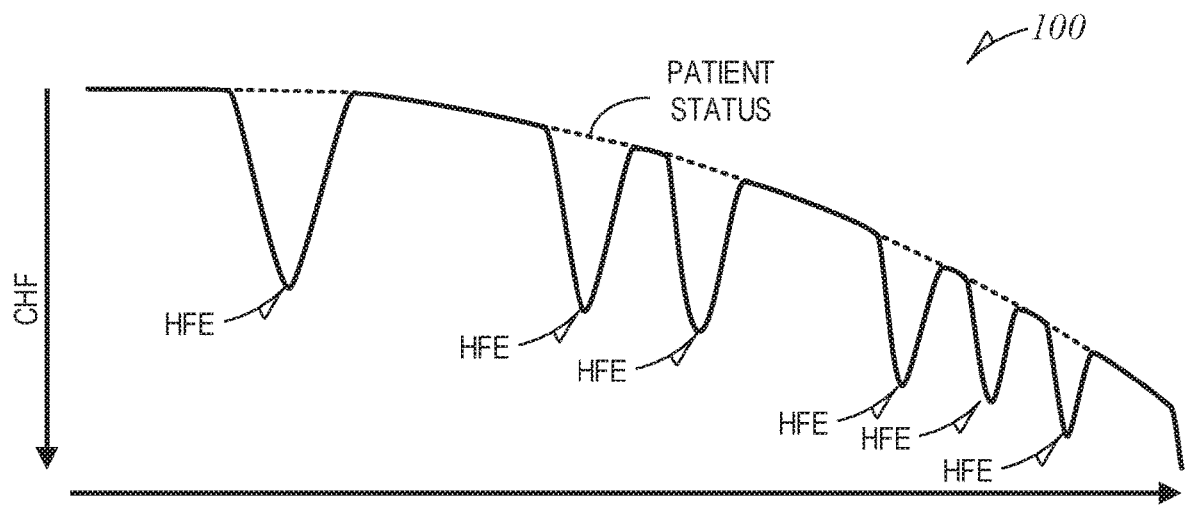
FIG. 1 illustrates an example patient status of a patient suffering from congestive heart failure (CHF) over time.

Ambulatory medical devices, including implantable, leadless, or wearable medical devices configured to monitor, detect, or treat various cardiac conditions resulting in a reduced ability of a heart to sufficiently deliver blood to a body, such as congestive heart failure (CHF). Various ambulatory medical devices can be implanted in a patient's body or otherwise positioned on or about the patient to monitor patient physiologic information, such as heart sounds, respiration (e.g., respiration rate, tidal volume, etc.), impedance (e.g., thoracic impedance), pressure, cardiac activity (e.g., heart rate), physical activity, or one or more other physiological parameters of a patient, or to provide electrical stimulation or one or more other therapies or treatments to optimize or control contractions of the heart.

Traditional cardiac rhythm management (CRM) devices, such as pacemakers, defibrillators, or cardiac monitors, include subcutaneous devices implanted in a chest of a patient, having one or more leads to position one or more electrodes or other sensors at various locations in the heart, such as in one or more of the atria or ventricles. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the patient.

Leadless cardiac pacemakers (LCP) include small (e.g., smaller than traditional implantable CRM devices), self-contained devices configured to detect physiologic information from or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in the heart to detect physiologic information from, or provide one or more therapies or stimulation to, one or more chambers of the heart. The multiple LCP devices can communicate between themselves, or one or more other implanted or external devices.

In contrast, wearable or external medical sensors or devices can be configured to detect or monitor physiologic information of the patient without required implant or an in-patient procedure for placement, battery replacement, or repair. However, such sensors and devices, in contrast to implantable, subcutaneous, or leadless medical devices, can suffer from reduced patient compliance, increased detection noise, or reduced detection sensitivity.

Risk stratification for CHF often requires some initial assessment time to establish a baseline level or condition from one or more sensors or physiologic information which to detect deviation from and determine a risk of a heart failure event (HFE), or from which to predict or stratify the risk of the patient experiencing an HFE in a following period. Changes in physiologic information can be aggregated and weighted based on one or more patient-specific stratifiers. However, such changes and risk stratification are often associated with one or more thresholds, for example, having a clinical sensitivity and specificity across a target population with respect to a specific condition (e.g., CHF), etc., and one or more specific time periods, such as daily values, short term averages (e.g., daily values aggregated over a number of days), long term averages (e.g., daily values aggregated over a number of short term periods or a greater number of days (sometimes different days than used for the short term average)), etc.

The present inventors have recognized, among other things, that thresholds, parameters, or sensor weightings used to determine a risk of worsening congestive heart failure (CHF) in a patient or across a patient population can be optimized using a count or ratio of heart failure events (HFE) occurring in inside (IN) or outside (OUT) of an alert state, improving the sensitivity and specificity of existing sensors in predicting or assessing CHF, and diverting existing resources to patients in more immediate need of intervention.

Physiologic information from a patient can be evaluated to identify a patient alert state, such as alert states associated with a specified risk of CHF, a level associated with one or more signal metrics generated using at least a portion of the patient physiologic information, etc. Alert states can include inside (IN) an alert state, outside (OUT) an alert state, or one or more other intermediate or other alert states. One or more heart failure events (HFEs) can be determined using the patient physiologic information, or using information about a patient admission or hospitalization, or a treatment or intervention associated with a congestive heart failure condition. HFE rates can be calculated in the one or more alert states. Further, one or more event rate ratios (ERRs) can be calculated as a ratio of event rates in one or more different alert states. For example, an event rate ratio (ERR) can be calculated as a ratio of event rates during IN versus OUT alert states.

FIG. 1 illustrates an example patient status 100 of a patient suffering from congestive heart failure (CHF) over time. The dashed line represents a decline in patient CHF status, with the individual dips representing heart failure events (HFEs) occurring as the patient status declines. In other examples, the overall status can incline or decline in the presence of more or less HFEs. In an example, HFEs can be include patient admissions or unscheduled visits into a hospital or clinic for heart failure treatment. In other examples, HFEs can include sudden, acute changes in patient physiologic information or status. In an example, an HFE can be detected, or the severity of an HFE can be determined, using one or more detected biomarkers, such as a natriuretic peptide, a B-type natriuretic peptide (BNP), an N-terminal proBNP (NT-proBNP), etc.

Figure 2:
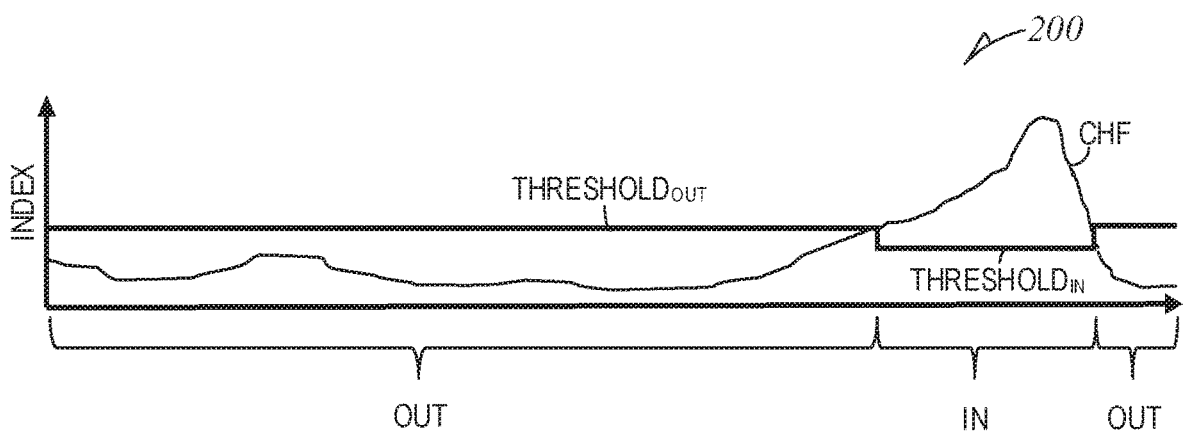
FIG. 2 illustrates an example congestive heart failure (CHF) index over time and one or more thresholds.

FIG. 2 illustrates an example congestive heart failure (CHF) index over time and one or more thresholds. The CHF index can be indicative of the patient CHF status. In FIG. 1, a decrease in patient status indicated worsening CHF. In this example, an increase in the CHF index indicates a worsening CHF status, or an increased risk of a worsening CHF status or impending CHF event. In this example, when the CHF index is below a threshold, the patient can be determined to be in an OUT alert state; when the CHF index is above a threshold, the patient can be determined to be in an IN alert state.

The thresholds in FIG. 2 include an OUT threshold ($THRESHOLD_{OUT}$) in the OUT alert state, and an IN threshold ($THRESHOLD_{IN}$) in the IN alert state. The IN threshold can be different than the OUT threshold to provide hysteresis to avoid sudden state changes. In other examples, one or more other or additional thresholds or states can be provided (e.g., an Intermediate alert state, etc.).

In an example, the CHF index and thresholds can include an index, score, or other metric or measure that indicates a CHF condition of a patient, such as described in one or more of the commonly assigned: Qi An et al., U.S. application Ser. No. 14/510,392, titled "Methods and apparatus for detecting heart failure decompensation event and stratifying the risk of the same"; Robert. J. Sweeney et al., U.S. application Ser. No. 14/282,353, titled "Methods and apparatus for stratifying risk of heart failure decompensation"; Qi An et al. U.S. application Ser. No. 13/726,786, titled "Risk stratification based heart failure detection algorithm", each of which is incorporated herein by reference in their entirety.

In an example, an event rate (ER) can be determined for each alert state by counting individual heart failure events (HFEs) in each alert state. For example, an ER for the OUT alert state ($ER_{OUT}$) or the IN alert state ($ER_{IN}$) can be determined as the number of HFEs in the specific alert state, over the time the patient is in the alert state (e.g., number of days in the specific alert state, etc.), such as illustrated in equations (1) and (2):

$$ER_{OUT} = \frac{\text{\# Events while OUT alert state}}{\text{\# Days OUT alert state}} \quad (1)$$

$$ER_{IN} = \frac{\text{\# Events while IN alert state}}{\text{\# Days IN alert state}} \quad (2)$$

In an example, one or more event rate ratios (ERRs) can be determined using a ratio of the event rates across one or more alert states, such as illustrated in equation (3):

$$ERR = \frac{ER_{IN}}{ER_{OUT}} \quad (3)$$

Figure 3:
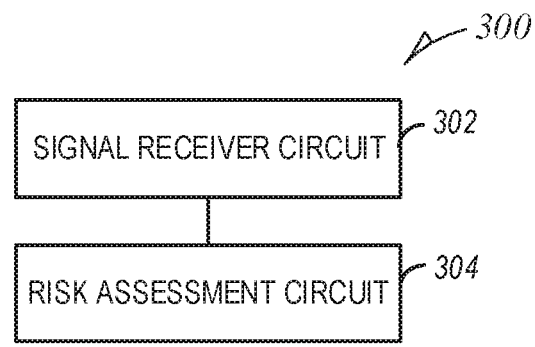
FIG. 3 illustrates an example system including a signal receiver circuit and a risk assessment circuit.

FIG. 3 illustrates an example system (e.g., a medical device, etc.) 300 including a signal receiver circuit 302 and a risk assessment circuit 304. The signal receiver circuit 302 can be configured to receive patient information, such as physiologic information of a patient or group of patients. The risk assessment circuit 304 can be configured to determine an alert state of a patient using the received physiologic information, to determine an event rate for the patient or the group of patients for each alert state, and to adjust a composite worsening heart failure (HF) risk calculation for the patient or group of patients using the determined event rates. In certain examples, the signal receiver circuit 302 can be configured to receive a count of heart failure events (HFEs) for a patient or a group of patients from a user, a clinician, medical records, etc. In other examples, the system 300 can receive an indication of an intervention associated with congestive heart failure (CHF), and store a count of individual HFEs associated with the patient or the group of patients. In an example, risk assessment circuit 304 can determine the event rate for the patient or the group of patients for each alert state using the received HFEs.

The worsening HF risk calculation can include a composite CHF risk indicator determined using a combination of physiological data that change in response to cardiac decompensation, including one or more of a first heart sound, a third heart sound, respiration rate, respiration volume, thoracic impedance, heart rate, or daily patient activity. In certain examples, the individual sensor inputs can be stratified, or one or more sensor weightings can be adjusted depending on the values of one or more other physiologic parameters. In other examples, the physiologic data can include one or more biomarkers detected from the patient.

In an example, the risk assessment circuit 304 can be configured to adjust one or more thresholds (e.g., CHF thresholds, etc.), or individual sensor or parameter weightings to optimize one or more of an event rate or event rate ratio. For example, a heart failure threshold or parameter can be adjusted to minimize an OUT alert state event rate ($ER_{OUT}$), to minimize an IN alert state event rate ($ER_{IN}$), or to maximize or minimize an event rate ratio (e.g., maximize $ERR_{IN}/ERR_{OUT}$, etc.).

In other examples, the risk assessment circuit 304 can be configured to provide an output to a user, such as to a display or one or more other user interface, the output including event rate or event rate ratio information, or a recommendation to a user to adjust a threshold or sensor weighting to optimize one or more of an event rate or event rate ratio, or to provide a desired outcome (e.g., limit a number of OUT alert heart failure events (HFEs) to a specified number or rate, etc.). In other examples, the event rate or event rate ratio information can be provided to a user in addition to other threshold or patient physiologic information.

In certain examples, the signal receiver circuit 302 can be configured to receive information from a plurality of patients, and the risk assessment circuit 304 can be configured to determine high risk patients from the plurality of patients using determined event rates or event rate ratios for the plurality of patients. For example, the risk assessment circuit 304 can be configured to adjust a weighting of one or more sensors in a composite CHF risk indicator indicative of a risk of worsening heart failure to optimize an event rate or an event rate ratio of a specific patient or a group of patients, such as to help identify those patients in the group having the highest risk of worsening heart failure, or to determine a risk of worsening heart failure of a specific patient.

Figure 4:
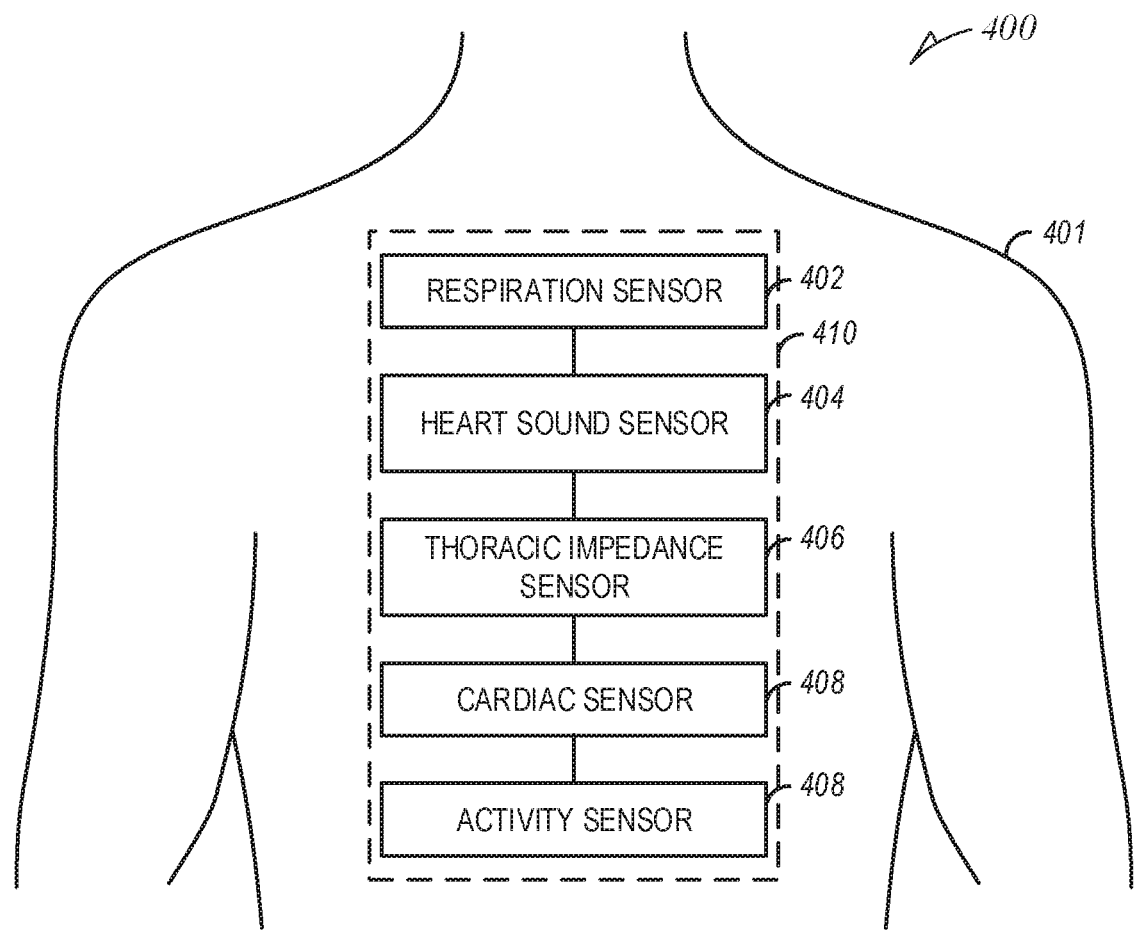
FIG. 4 illustrates an example system including an ambulatory medical device (AMD) configured to sense or detect information from a patient.

FIG. 4 illustrates an example system 400 including an ambulatory medical device (AMD) 410 configured to sense or detect information from a patient 401. In an example, the AMD 410 can include an implantable medical device (IMD), a subcutaneous or leadless medical device, a wearable or external medical device, or one or more other implantable or external medical devices or patient monitors. The AMD 410 can include a single device, or a plurality of medical devices or monitors configured to detect patient information.

The AMD 410 can include a respiration sensor 402 configured to receive respiration information (e.g., a respiration rate (RR), a respiration volume (tidal volume), etc.) of the patient 401, a heart sound sensor 404 configured to receive heart sound information of the patient 401, a thoracic impedance sensor 406 configured to receive impedance information from the patient 401, a cardiac sensor 408 configured to receive cardiac electrical information from the patient 401, and an activity sensor 408 configured to receive information about a physical motion (e.g., activity, posture, etc.) of the patient 401, or one or more other sensors configured to receive physiologic information of the patient 401.

In an example, the sensors in the AMD 410 include existing physiologic sensors. However, using the system and methods described herein, the sensitivity and specificity of one or more metrics associated with a risk of worsening congestive heart failure (CHF) detected using existing sensors can be increased without otherwise increasing system cost or power, or negatively affecting usable battery life of the existing sensors.

Figure 5:
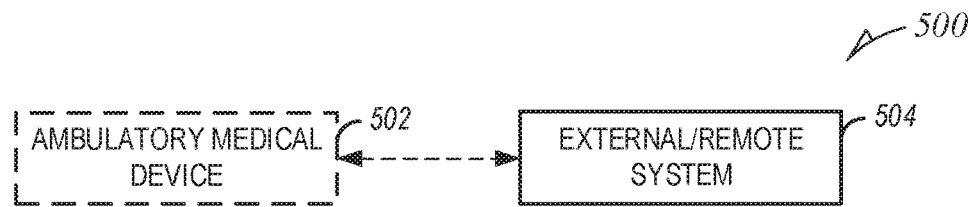
FIG. 5 illustrates an example system including an ambulatory medical device (AMD) coupled to an external or remote system.

FIG. 5 illustrates an example system 500 including an ambulatory medical device (AMD) 502 coupled to an external or remote system 504, such as an external programmer. In an example, the AMD 502 can be an implantable device, an external device, or a combination or permutation of one or more implantable or external devices. In an example, one or more of the signal receiver circuit 302 or the risk assessment circuit 304 can be located in the AMD 502, or the remote system 504. The remote system 504 can include a specialized device configured to interact with the AMD 502, including to program or receive information from the AMD 502.

Figure 6:
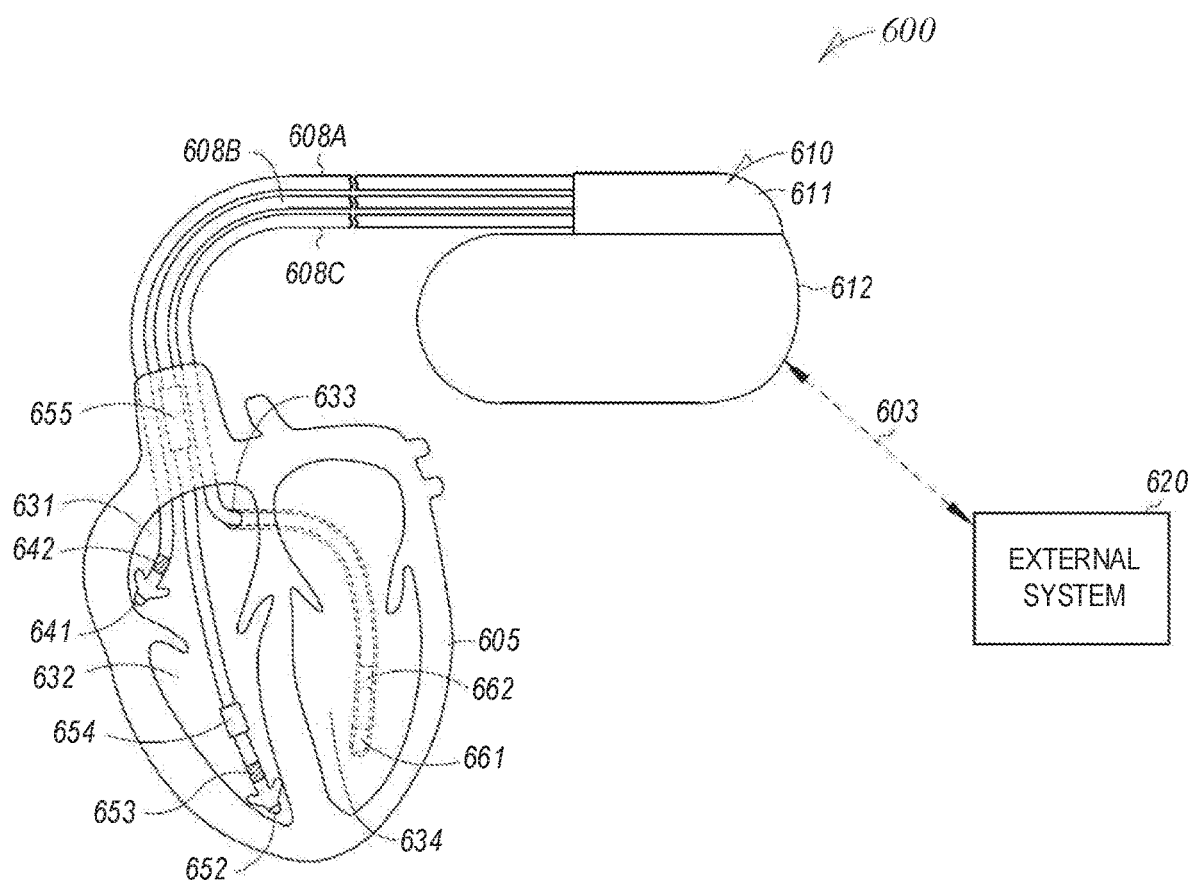
FIG. 6 illustrates an example of a Cardiac Rhythm Management (CRM) system.

FIG. 6 illustrates an example of a Cardiac Rhythm Management (CRM) system 600 and portions of an environment in which the CRM system 600 can operate. The CRM system 600 can include an ambulatory medical device, such as an implantable medical device (IMD) 610 that can be electrically coupled to a heart 605 such as through one or more leads 608A-C coupled to the IMD 610 using a header 611, and an external system 620 that can communicate with the IMD 610 such as via a communication link 603. The IMD 610 may include an implantable cardiac device such as a pacemaker, an implantable cardioverter-defibrillator (ICD), or a cardiac resynchronization therapy defibrillator (CRT-D). The IMD 610 can include one or more monitoring or therapeutic devices such as a subcutaneously implanted device, a wearable external device, a neural stimulator, a drug delivery device, a biological therapy device, or one or more other ambulatory medical devices. The IMD 610 may be coupled to, or may be substituted by a monitoring medical device such as a bedside or other external monitor.

As illustrated in FIG. 6, the IMD 610 can include a hermetically sealed can 612 that can house an electronic circuit that can sense a physiological signal in the heart 605 and can deliver one or more therapeutic electrical pulses to a target region, such as in the heart, such as through one or more leads 608A-C. In certain examples, the CRM system 600 can include only a single lead, such as 608B, or can include only two leads, such as 608A and 608B.

The lead 608A can include a proximal end that can be configured to be connected to IMD 610 and a distal end that can be configured to be placed at a target location such as in the right atrium (RA) 631 of the heart 605. The lead 608A can have a first pacing-sensing electrode 641 that can be located at or near its distal end, and a second pacing-sensing electrode 642 that can be located at or near the electrode 641. The electrodes 641 and 642 can be electrically connected to the IMD 610 such as via separate conductors in the lead 608A, such as to allow for sensing of the right atrial activity and optional delivery of atrial pacing pulses. The lead 608B can be a defibrillation lead that can include a proximal end that can be connected to IMD 610 and a distal end that can be placed at a target location such as in the right ventricle (RV) 632 of heart 605. The lead 608B can have a first pacing-sensing electrode 652 that can be located at distal end, a second pacing-sensing electrode 653 that can be located near the electrode 652, a first defibrillation coil electrode 654 that can be located near the electrode 653, and a second defibrillation coil electrode 655 that can be located at a distance from the distal end such as for superior vena cava (SVC) placement. The electrodes 652 through 655 can be electrically connected to the IMD 610 such as via separate conductors in the lead 608B. The electrodes 652 and 653 can allow for sensing of a ventricular electrogram and can optionally allow delivery of one or more ventricular pacing pulses, and electrodes 654 and 655 can allow for delivery of one or more ventricular cardioversion/defibrillation pulses. In an example, the lead 608B can include only three electrodes 652, 654, and 655. The electrodes 652 and 654 can be used for sensing or delivery of one or more ventricular pacing pulses, and the electrodes 654 and 655 can be used for delivery of one or more ventricular cardioversion or defibrillation pulses. The lead 608C can include a proximal end that can be connected to the IMD 610 and a distal end that can be configured to be placed at a target location such as in a left ventricle (LV) 634 of the heart 605. The lead 608C may be implanted through the coronary sinus 633 and may be placed in a coronary vein over the LV such as to allow for delivery of one or more pacing pulses to the LV. The lead 608C can include an electrode 661 that can be located at a distal end of the lead 608C and another electrode 662 that can be located near the electrode 661. The electrodes 661 and 662 can be electrically connected to the IMD 610 such as via separate conductors in the lead 608C such as to allow for sensing of the LV electrogram and optionally allow delivery of one or more resynchronization pacing pulses from the LV.

The IMD 610 can include an electronic circuit that can sense a physiological signal. The physiological signal can include an electrogram or a signal representing mechanical function of the heart 605. The hermetically sealed can 612 may function as an electrode such as for sensing or pulse delivery. For example, an electrode from one or more of the leads 608A-C may be used together with the can 612 such as for unipolar sensing of an electrogram or for delivering one or more pacing pulses. A defibrillation electrode from the lead 608B may be used together with the can 612 such as for delivering one or more cardioversion/defibrillation pulses. In an example, the IMD 610 can sense impedance such as between electrodes located on one or more of the leads 608A-C or the can 612. The IMD 610 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 610 can be configured to inject current between an electrode on the RV lead 608B and the can 612, and to sense the resultant voltage between the same electrodes or between a different electrode on the RV lead 608B and the can 612. A physiologic signal can be sensed from one or more physiological sensors that can be integrated within the IVID 610. The IMD 610 can also be configured to sense a physiological signal from one or more external physiologic sensors or one or more external electrodes that can be coupled to the ID 610. Examples of the physiological signal can include one or more of heart rate, heart rate variability, intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are.

The CRM system 600 can include a patient chronic condition-based HF risk assessment circuit, such as illustrated in the commonly assigned Qi An et al., U.S. application Ser. No. 14/510,392, titled "Methods and apparatus for detecting heart failure decompensation event and stratifying the risk of the same," incorporated herein by reference in its entirety. The patient chronic condition-based HF risk assessment circuit can include a signal analyzer circuit and a risk stratification circuit. The signal analyzer circuit can receive patient chronic condition indicators and one or more physiologic signals from the patient, and select one or more patient-specific sensor signals or signal metrics from the physiologic signals. The signal analyzer circuit can receive the physiologic signals from the patient using the electrodes on one or more of the leads 608A-C, or physiologic sensors deployed on or within the patient and communicated with the IMD 610. The risk stratification circuit can generate a composite risk index indicative of the probability of the patient later developing an event of worsening of HF (e.g., an HF decompensation event) such as using the selected patient-specific sensor signals or signal metrics. The HF decompensation event can include one or more early precursors of an HF decompensation episode, or an event indicative of HF progression such as recovery or worsening of HF status.

The external system 620 can allow for programming of the IMD 610 and can receives information about one or more signals acquired by IMD 610, such as can be received via a communication link 603. The external system 620 can include a local external IMD programmer. The external system 620 can include a remote patient management system that can monitor patient status or adjust one or more therapies such as from a remote location.

The communication link 603 can include one or more of an inductive telemetry link, a radio-frequency telemetry link, or a telecommunication link, such as an internet connection. The communication link 603 can provide for data transmission between the IMD 610 and the external system 620. The transmitted data can include, for example, real-time physiological data acquired by the IMD 610, physiological data acquired by and stored in the IMD 610, therapy history data or data indicating IMD operational status stored in the IMD 610, one or more programming instructions to the IMD 610 such as to configure the IMD 610 to perform one or more actions that can include physiological data acquisition such as using programmably specifiable sensing electrodes and configuration, device self-diagnostic test, or delivery of one or more therapies.

The patient chronic condition-based HF risk assessment circuit may be implemented at the external system 620, which can be configured to perform HF risk stratification such as using data extracted from the IMD 610 or data stored in a memory within the external system 620. Portions of patient chronic condition-based HF risk assessment circuit may be distributed between the IMD 610 and the external system 620.

Portions of the IMD 610 or the external system 620 can be implemented using hardware, software, or any combination of hardware and software. Portions of the IMD 610 or the external system 620 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 610, the CRM system 600 could include a subcutaneous medical device (e.g., subcutaneous ICD, subcutaneous diagnostic device), wearable medical devices (e.g., patch based sensing device), or other external medical devices.

Figure 7A:
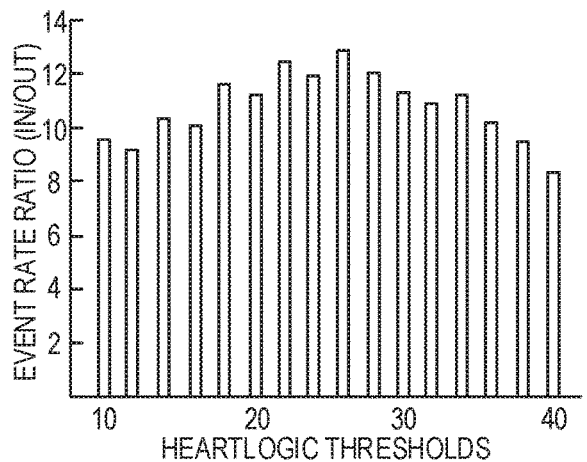
FIGS. 7A-7B illustrate example event rate ratios (ERRs) for congestive heart failure (CHF) metrics.
Figure 7B:
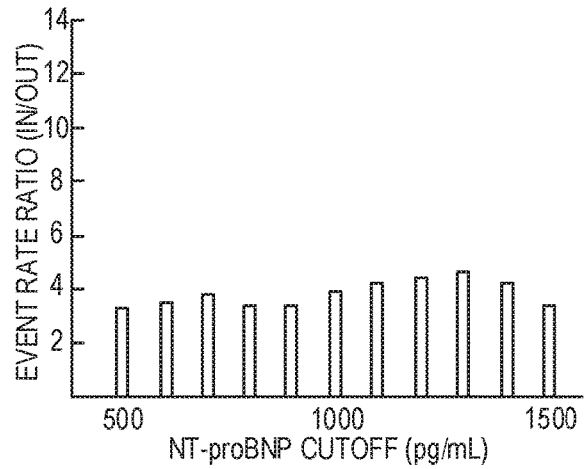

FIGS. 7A-7B illustrate example event rate ratios (ERRs) for two congestive heart failure (CHF) metrics. FIG. 7A illustrates example ERRs ($ERR_{IN}/ERR_{OUT}$) across a range of programmable HeartLogic thresholds. The HeartLogic risk indicator is a composite CHF risk indicator determined using a combination of physiological data that change in response to cardiac decompensation: heart sounds (including S1 and S3), respiration rate and volume, thoracic impedance, heart rate and daily patient activity.

FIG. 7B illustrates example ERRs (High/Low) across a range of N-terminal pro B-type natriuretic peptide (NT-proBNP) thresholds. NT-pro-BNP is a biomarker indicative of adverse outcome in heart failure patients. Event rates for the NT-proBNP metric were calculated as HIGH if the HFE was associated with a biomarker concentration at or over the defined threshold, and LOW if the HFE was associated with a biomarker concentration below the defined threshold.

Figure 8A:
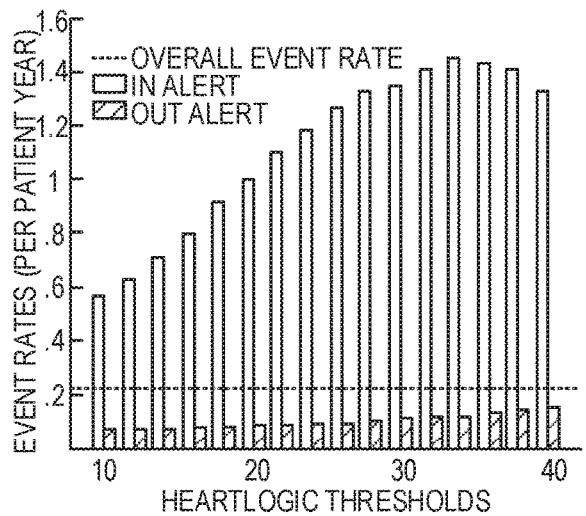
FIGS. 8A-8B illustrate example event rates (ERs) per patient year for congestive heart failure (CHF) metrics.
Figure 8B:
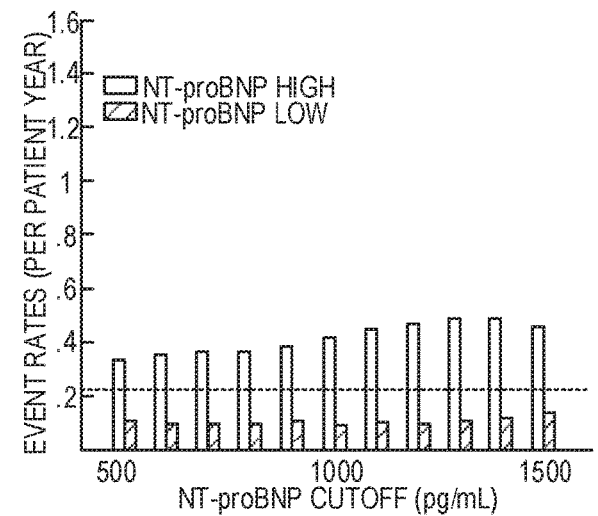

FIGS. 8A-8B illustrate example event rates (ERs) per patient year for two congestive heart failure (CHF) metrics. FIG. 8A illustrates example ERs for patients IN alert state and separately for patients OUT alert state across a range of programmable HeartLogic thresholds. FIG. 8B illustrates example ERs across a range of NT-proBNP thresholds.

Figure 9A:
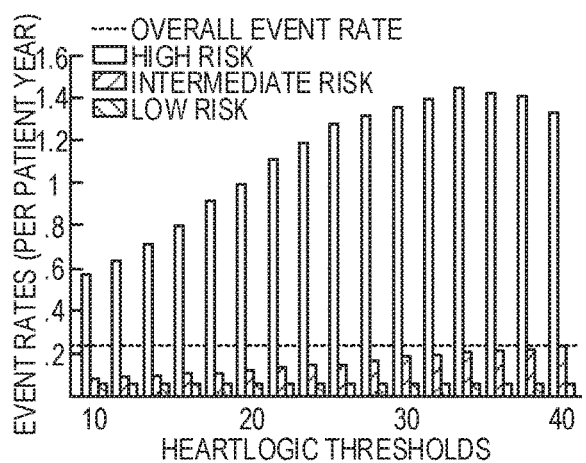
FIG. 9A illustrates example event rates (ERs) per patient year for multiple patient risk groups across a range of programmable thresholds.

FIG. 9A illustrates example event rates (ERs) per patient year for multiple patient risk groups across a range of programmable HeartLogic thresholds. The multiple patient risk groups include high risk, intermediate risk, and low risk patient groups. High risk patient groups include those having a HeartLogic level above the threshold. Intermediate risk patient groups include those having a HeartLogic level between the threshold and a small value (e.g., 2). Low risk patient groups include those having a HeartLogic level lower than the small value (e.g., 2). Significant resources are directed to the low risk patient group, (e.g., 41%) that can be directed elsewhere.

Figure 9B:
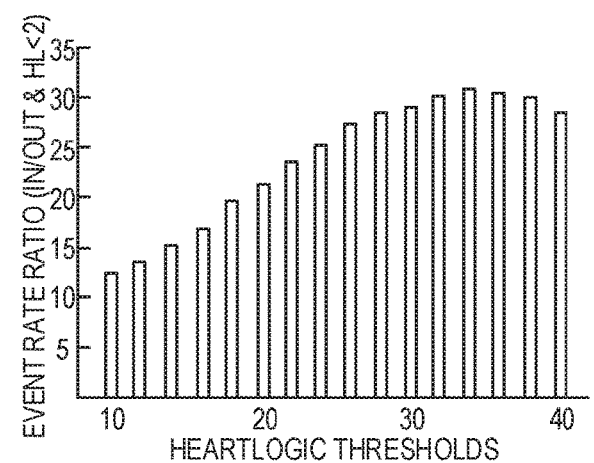
FIG. 9B illustrates example event rate ratios (ERRs) between the high risk and low risk groups across a range of programmable thresholds.

FIG. 9B illustrates example event rate ratios (ERRs) between the high risk and low risk groups of FIG. 9A across a range of programmable HeartLogic thresholds. As illustrated, the ER for the high risk groups range from 12 to 31 times higher than the low risk groups.

The HeartLogic CHF risk indicator, across any threshold between 10 and 40, has a higher likelihood of predicting a heart failure event (HFE) than other biomarkers or clinical variables.

TABLE 1

Multivariate Analysis of Predictors of Event Rates.

| Clinical Variable | Event Rate Ratio (95% CI) | p-value |
|---|---|---|
| HeartLogic ≥ 10 | 5.06 (3.17, 8.08) | <.0001 |
| HeartLogic ≥ 12 | 5.20 (3.26, 8.30) | <.0001 |
| HeartLogic ≥ 14 | 5.48 (3.40, 8.84) | <.0001 |
| HeartLogic ≥ 16 | 5.91 (3.63, 9.62) | <.0001 |
| HeartLogic ≥ 18 | 6.51 (3.98, 10.65) | <.0001 |
| HeartLogic ≥ 20 | 6.35 (4.10, 9.85) | <.0001 |
| HeartLogic ≥ 22 | 7.00 (4.49, 10.92) | <.0001 |
| HeartLogic ≥ 24 | 6.80 (4.39, 10.52) | <.0001 |
| HeartLogic ≥ 26 | 7.44 (4.69, 11.80) | <.0001 |
| HeartLogic ≥ 28 | 7.53 (4.68, 12.11) | <.0001 |
| HeartLogic ≥ 30 | 6.27 (3.88, 10.15) | <.0001 |
| HeartLogic ≥ 32 | 6.25 (3.91, 9.99) | <.0001 |
| HeartLogic ≥ 34 | 5.71 (3.74, 8.73) | <.0001 |
| HeartLogic ≥ 36 | 4.77 (3.14, 7.25) | <.0001 |
| HeartLogic ≥ 38 | 4.72 (3.03, 7.34) | <.0001 |
| HeartLogic ≥ 40 | 4.18 (2.71, 6.43) | <.0001 |
| NT Pro-BNP ≥ 1000 pg/mL | 2.40 (1.29, 4.46)* | 0.0055* |
| History of AF or AFl | 2.34 (1.32, 4.14)* | 0.0036* |
| History of renal disease | 2.30 (1.40, 3.79)* | 0.0010* |
| NYHA III or IV | 2.17 (1.21, 3.88)* | 0.0094* |
| Total plasma protein ≥ 7.1 | 1.78 (1.03, 3.08)* | 0.0377* |
| Sodium ≥ 140 | 1.33 (0.80, 2.21)* | 0.2747* |
| LVEF ≥ 28 | 1.11 (0.69, 1.79)* | 0.6751* |
| Diabetes | 1.11 (0.67, 1.83)* | 0.6871* |

In other examples, other variables can include, separately or in combination with one or more of the variables in Table 1, above, one or more of: age, gender, body mass index (BMI), blood pressure (BP) (e.g., systolic, diastolic, etc.), total hemoglobin, prior myocardial infarction (MI), K+ level, NA+ level, creatine, blood urea nitrogen (BUN), etc.

Event Rae Ratio (ERR) and p-values for clinical variables* were calculated at HeartLogic threshold of 16.

The robustness of the HeartLogic indicator is further evidenced across a range of NT-proBNP thresholds.

TABLE 2

Robustness of HeartLogic versus NT-proBNP Across Thresholds.

| HL Threshold | NT-proBNP Cut-off | | | | | | | | | | |
|---|---|---|---|---|---|---|---|---|---|---|---|
| | 500 | 600 | 700 | 800 | 900 | 1000 | 1100 | 1200 | 1300 | 1400 | 1500 |
| 10 | 0.0138 | 0.0108 | 0.0108 | 0.0020 | 0.0015 | 0.0018 | 0.0017 | 0.0023 | 0.0025 | 0.0015 | 0.0006 |
| 12 | 0.0184 | 0.0146 | 0.0146 | 0.0030 | 0.0023 | 0.0027 | 0.0025 | 0.0032 | 0.0034 | 0.0021 | 0.0008 |
| 14 | 0.0170 | 0.0132 | 0.0129 | 0.0026 | 0.0019 | 0.0024 | 0.0022 | 0.0028 | 0.0029 | 0.0018 | 0.0007 |
| 16 | 0.0126 | 0.0097 | 0.0095 | 0.0019 | 0.0014 | 0.0018 | 0.0017 | 0.0021 | 0.0022 | 0.0013 | 0.0004 |
| 18 | 0.0095 | 0.0072 | 0.0071 | 0.0014 | 0.0012 | 0.0014 | 0.0014 | 0.0017 | 0.0018 | 0.0010 | 0.0003 |
| 20 | 0.0059 | 0.0042 | 0.0040 | 0.0007 | 0.0005 | 0.0007 | 0.0007 | 0.0009 | 0.0009 | 0.0005 | 0.0002 |
| 22 | 0.0055 | 0.0040 | 0.0039 | 0.0007 | 0.0006 | 0.0007 | 0.0007 | 0.0009 | 0.0009 | 0.0006 | 0.0002 |
| 24 | 0.0085 | 0.0061 | 0.0064 | 0.0014 | 0.0013 | 0.0017 | 0.0017 | 0.0021 | 0.0023 | 0.0016 | 0.0007 |
| 26 | 0.0097 | 0.0073 | 0.0080 | 0.0020 | 0.0020 | 0.0025 | 0.0025 | 0.0032 | 0.0035 | 0.0025 | 0.0012 |
| 28 | 0.0086 | 0.0067 | 0.0081 | 0.0024 | 0.0023 | 0.0031 | 0.0033 | 0.0044 | 0.0051 | 0.0036 | 0.0016 |
| 30 | 0.0081 | 0.0065 | 0.0083 | 0.0023 | 0.0036 | 0.0050 | 0.0054 | 0.0072 | 0.0082 | 0.0063 | 0.0030 |
| 32 | 0.0126 | 0.0109 | 0.0145 | 0.0048 | 0.0046 | 0.0068 | 0.0077 | 0.0103 | 0.0122 | 0.0090 | 0.0044 |
| 34 | 0.0124 | 0.0108 | 0.0146 | 0.0046 | 0.0045 | 0.0066 | 0.0075 | 0.0102 | 0.0122 | 0.0097 | 0.0048 |
| 36 | 0.0224 | 0.0205 | 0.0282 | 0.0101 | 0.0103 | 0.0149 | 0.0174 | 0.0232 | 0.0272 | 0.0212 | 0.0122 |
| 38 | 0.0256 | 0.0239 | 0.0323 | 0.0140 | 0.0147 | 0.0205 | 0.0241 | 0.0310 | 0.0358 | 0.0294 | 0.0204 |
| 40 | 0.0471 | 0.0456 | 0.0630 | 0.0296 | 0.0316 | 0.0442 | 0.0516 | 0.0666 | 0.0769 | 0.0639 | 0.0456 |

In other examples, HeartLogic and B-type natriuretic peptide (BNP) (or other biomarker) detection or alerts can be combined, increasing effectiveness of HF detection, or HF risk determination. For example, the event rate of patients having a HeartLogic score at or above a threshold (e.g., 16, etc.) and a biomarker (e.g., NT-proBNP) level at or above a threshold (e.g., NT-proBNP greater than or equal to 1000, etc.), is significantly higher than using the biomarker or the HeartLogic threshold alone. For example, using a biomarker alone, detected event rates (events per patient-year) below or greater than or equal to a threshold (e.g., NT-proBNP of 1000) were 0.11 and 0.42, respectively. Using HeartLogic alone, detected event rates below or greater than or equal to a threshold (e.g., Heartlogic of 16) were 0.08 and 0.8, respectively. However, combining the biomarker and HeartLogic detections, detected event rates for a HeartLogic score below a threshold (e.g., 16) and a biomarker below or greater than or equal to a threshold (e.g., NT-proBNP of 1000) were 0.02 and 0.16, respectively, and detected event rates for the HeartLogic score greater than or equal to the threshold (e.g., 16) and the biomarker below or greater than or equal to the threshold (e.g., NT-proBNP of 1000) were 0.47 and 1.00, respectively. The combination of biomarkers, and specifically BNP (e.g., NT-proBNP) and HeartLogic significantly augments the ability to identify patients having elevated risk of an HFE, in contrast to existing systems using HeartLogic or biomarkers alone. Such detection provides significant advantages for existing systems, improving the sensitivity and specificity of existing sensors in predicting or assessing CHF, and diverting existing resources to patients in more immediate need of intervention.

Figure 10:
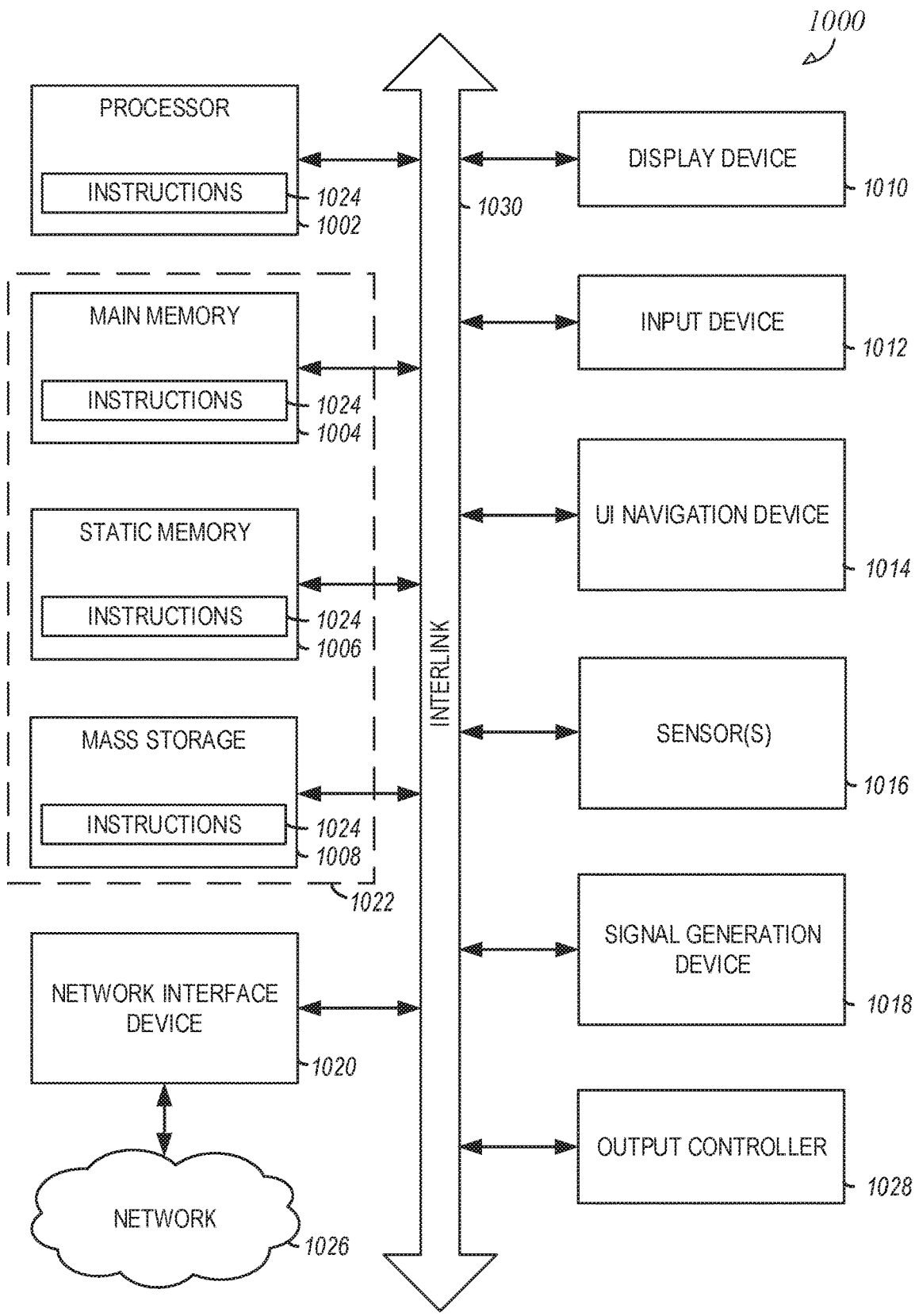
FIG. 10 illustrates a block diagram of an example machine upon which any one or more of the techniques discussed herein may perform.

FIG. 10 illustrates a block diagram of an example machine 1000 upon which any one or more of the techniques (e.g., methodologies) discussed herein may perform. Portions of this description may apply to the computing framework of one or more of the medical devices described herein, such as the IMD, the external programmer, etc.

Examples, as described herein, may include, or may operate by, logic or a number of components, or mechanisms in the machine 1000. Circuitry (e.g., processing circuitry) is a collection of circuits implemented in tangible entities of the machine 1000 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 1000 follow.

In alternative embodiments, the machine 1000 may operate as a standalone device or may be connected (e.g., networked) to other machines. In a networked deployment, the machine 1000 may operate in the capacity of a server machine, a client machine, or both in server-client network environments. In an example, the machine 1000 may act as a peer machine in peer-to-peer (P2P) (or other distributed) network environment. The machine 1000 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 1000 may include a hardware processor 1002 (e.g., a central processing unit (CPU), a graphics processing unit (GPU), a hardware processor core, or any combination thereof), a main memory 1004, a static memory (e.g., memory or storage for firmware, microcode, a basic-input-output (BIOS), unified extensible firmware interface (UEFI), etc.) 1006, and mass storage 1008 (e.g., hard drive, tape drive, flash storage, or other block devices) some or all of which may communicate with each other via an interlink (e.g., bus) 1030. The machine 1000 may further include a display unit 1010, an alphanumeric input device 1012 (e.g., a keyboard), and a user interface (UI) navigation device 1014 (e.g., a mouse). In an example, the display unit 1010, input device 1012, and UI navigation device 1014 may be a touch screen display. The machine 1000 may additionally include a signal generation device 1018 (e.g., a speaker), a network interface device 1020, and one or more sensors 1016, such as a global positioning system (GPS) sensor, compass, accelerometer, or other sensor. The machine 1000 may include an output controller 1028, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 1002, the main memory 1004, the static memory 1006, or the mass storage 1008 may be, or include, a machine-readable medium 1022 on which is stored one or more sets of data structures or instructions 1024 (e.g., software) embodying or utilized by any one or more of the techniques or functions described herein. The instructions 1024 may also reside, completely or at least partially, within any of registers of the processor 1002, the main memory 1004, the static memory 1006, or the mass storage 1008 during execution thereof by the machine 1000. In an example, one or any combination of the hardware processor 1002, the main memory 1004, the static memory 1006, or the mass storage 1008 may constitute the machine-readable medium 1022. While the machine-readable medium 1022 is illustrated as a single medium, the term "machine-readable medium" may include a single medium or multiple media (e.g., a centralized or distributed database, and/or associated caches and servers) configured to store the one or more instructions 1024.

The term "machine-readable medium" may include any medium that is capable of storing, encoding, or carrying instructions for execution by the machine 1000 and that cause the machine 1000 to perform any one or more of the techniques of the present disclosure, or that is capable of storing, encoding or carrying data structures used by or associated with such instructions. Non-limiting machine-readable medium examples may include solid-state memories, optical media, magnetic media, and signals (e.g., radio frequency signals, other photon based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1024 may be further transmitted or received over a communications network 1026 using a transmission medium via the network interface device 1020 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1020 may include one or more physical jacks (e.g., Ethernet, coaxial, or phone jacks) or one or more antennas to connect to the communications network 1026. In an example, the network interface device 1020 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1000, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system, comprising:
   a signal receiver circuit configured to receive physiologic information of a patient;
   a risk stratification circuit configured to determine a composite heart failure (HF) risk for the patient using a combination of signal metrics, the composite HF risk indicative of a risk of the patient to develop a HF decompensation event; and
   a risk assessment circuit configured to:
   determine one of a plurality of alert states for the patient using the received physiologic information and a threshold;

receive an indication of an occurrence of a HF event for the patient;

determine a HF event rate for each of the plurality of alert states, the HF event rate representing a count of HF events for a specific alert state per unit time; and adjust the determination of the composite HF risk for the patient using the determined HF event rates for each of the plurality of alert states to increase a sensitivity or a specificity of the physiologic information in assessing the risk of the patient to develop the HF decompensation event.

2. The system of claim 1, wherein the indication of the occurrence of the HF event for the patient includes an indication of HF treatment to the patient.

3. The system of claim 2, wherein the indication of treatment to the patient includes an admission or unscheduled visit into a hospital or clinic for HF treatment or an indication that the patient received HF treatment.

4. The system of claim 1,
wherein to adjust the determination of the composite HF risk for the patient includes to adjust the combination of signal metrics or a weighting of a signal metric of the combination of signal metrics used to determine the composite HF risk.

5. The system of claim 1, wherein the plurality of alert states are HF alert states,
wherein the plurality of HF alert states includes an IN alert state and an OUT alert state,
wherein to determine the HF event rate for each of the plurality of HF alert states includes to determine an IN alert state HF event rate and an OUT alert state HF event rate, and
wherein to adjust the determination of the composite HF risk includes using the determined IN alert state HF event rate and the determined OUT alert state HF event rate.

6. The system of claim 5, wherein the risk assessment circuit is configured to determine a HF event rate ratio using a ratio of the determined IN alert state HF event rate and the determined OUT alert state HF event rate, and
wherein to adjust the determination of the composite HF risk includes using the HF event rate ratio.

7. The system of claim 6, wherein the HF event rate ratio is the determined IN alert state HF event rate divided by the determined OUT alert state HF event rate.

8. The system of claim 6, wherein to adjust the determination of the composite HF risk includes to adjust the threshold to maximize the HF event rate ratio.

9. The system of claim 5, wherein, to adjust the determination of the composite HF risk for the patient, the risk assessment circuit is configured to adjust the threshold to minimize the OUT alert state HF event rate or to minimize an IN alert state HF event rate.

10. The system of claim 1, wherein the received physiologic information includes a sensor input, and wherein to adjust the determination of the composite HF risk for the patient includes to adjust the sensor input or a weighting of the sensor input using the determined HT event rates for each of the plurality of alert states.

11. A method, comprising:
receiving physiologic information for a patients using a signal receiver circuit;
determining a composite heart failure (HF) risk for the patient using a combination of signal metrics, the composite HF risk indicative of a risk of the patient to develop a HF decompensation event;
determining, using a risk assessment circuit, one of a plurality of alert states for the patient using the received physiologic information and a threshold;
receiving, using the risk assessment circuit, an indication of an occurrence of a HF event for the patient;
determining, using the risk assessment circuit, a HF event rate for each of the plurality of alert states, the HF event rate representing a count of HF events for a specific alert state per unit time; and
adjusting, using the risk assessment circuit, the determination of the composite HF risk for the patient using the determined HF event rates for each of the plurality of alert states to increase a sensitivity or a specificity of the physiologic information in assessing the risk of the patient to develop the HF decompensation event.

12. The method of claim 11, wherein the indication of the occurrence of the HF event for the patient includes an indication of HF treatment to the patient.

13. The method of claim 12, wherein the indication of HF treatment to the patient includes an admission or unscheduled visit into a hospital or clinic for HF treatment or an indication that the patient received HT treatment.

14. The method of claim 11,
wherein adjusting the determination of the composite HF risk for the patient includes adjusting the combination of signal metrics or a weighting of a signal metric of the combination of signal metrics used to determine the composite HF risk.

15. The method of claim 11, wherein the plurality of alert states are HF alert states,
wherein the plurality of HF alert states includes an IN alert state and an OUT alert state,
wherein determining the HF event rate for each of the plurality of alert states includes determining an IN alert state HF event rate and an OUT alert state HF event rate, and
wherein adjusting the determination of the composite HF risk includes using the determined IN alert state HF event rate and the determined OUT alert state HF event rate.

16. The method of claim 15, comprising determining a HF event rate ratio using a ratio of the determined IN alert state HF event rate and the determined OUT alert state HF event rate,
wherein adjusting the determination of the composite HF risk includes using the HF event rate ratio.

17. The method of claim 16, wherein the HF event rate ratio is the determined IN alert state HF event rate divided by the determined OUT alert state HF event rate.

18. The method of claim 16, wherein adjusting the determination of the composite HF risk includes adjusting the threshold to maximize the HF event rate ratio.

19. The method of claim 15, wherein adjusting the determination of the composite HF risk includes adjusting the threshold to minimize the OUT alert state HF event rate or to minimize an IN alert state HF event rate.

20. The method of claim 11, wherein the received physiologic information includes a sensor input, and wherein adjusting the determination of the composite HF risk for the patient includes adjusting the sensor input or a weighting of the sensor input using the determined HF event rates for each of the plurality of alert states.

* * * * *